(12) United States Patent
Skardal

(10) Patent No.: US 11,047,847 B2
(45) Date of Patent: Jun. 29, 2021

(54) METHODS AND APPARATUS FOR MODELING CANCER METASTASIS IN VITRO

(71) Applicant: Wake Forest University Health Sciences, Winston-Salem, NC (US)

(72) Inventor: Aleksander Skardal, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 393 days.

(21) Appl. No.: 15/765,085

(22) PCT Filed: Sep. 30, 2016

(86) PCT No.: PCT/US2016/054611
§ 371 (c)(1),
(2) Date: Mar. 30, 2018

(87) PCT Pub. No.: WO2017/059173
PCT Pub. Date: Apr. 6, 2017

(65) Prior Publication Data
US 2018/0348203 A1    Dec. 6, 2018

Related U.S. Application Data

(60) Provisional application No. 62/241,872, filed on Oct. 15, 2015, provisional application No. 62/236,361, filed on Oct. 2, 2015.

(51) Int. Cl.
*G01N 33/50* (2006.01)
*C12M 1/00* (2006.01)
(52) U.S. Cl.
CPC ......... *G01N 33/5011* (2013.01); *C12M 23/22* (2013.01); *C12M 23/58* (2013.01); *C12M 29/00* (2013.01)

(58) Field of Classification Search
CPC ... G01N 33/5011; C12M 23/22; C12M 23/58; C12M 29/00; C12M 29/20; C12M 21/08;
(Continued)

(56) References Cited

U.S. PATENT DOCUMENTS 4,734,372 A      3/1988  Rotman
2007/0275363 A1* 11/2007  Bertram ................ C12M 37/04
                                                              435/1.2
(Continued)

FOREIGN PATENT DOCUMENTS

JP    2007515949 A    6/2007
JP    2015167521      2/2014
(Continued)

OTHER PUBLICATIONS

Rasheena Edmondson, Jessica Jenkins Broglie, Audrey F. Adcock and Ligu Yang. "Three-Dimensional Cell Culture Systems and Their Applications in Drug Discovery and Cell-Based Biosensors". Assay Drug Development Technologies. May 1, 2014; 12(4): 207-218. (Year: 2014).*

(Continued)

*Primary Examiner* — Michael L Hobbs
(74) *Attorney, Agent, or Firm* — Myers Bigel, P.A.

(57) ABSTRACT

An apparatus useful for examining metastasis of cancer cells, includes (a) a primary chamber; (b) at least one secondary chamber; (c) at least one primary conduit connecting said primary and secondary chambers and providing fluid communication therebetween; (d) a primary organoid in said first chamber, said primary organoid comprising mammalian cancer cells; (e) at least one secondary organoid separately selected for and in said secondary chamber(s); and (f) optionally a growth media in said primary chamber, each of said secondary chamber(s), and said primary con-
(Continued)

duit. The apparatus may be used in methods of drug screening and development, and in personalized medicine.

21 Claims, 11 Drawing Sheets

(58) Field of Classification Search
CPC ............... C12M 27/18; B01L 2200/10; B01L 2200/0647; B01L 2300/0861; B01L 3/502761
See application file for complete search history.

(56) References Cited

U.S. PATENT DOCUMENTS

| | | | |
|---|---|---|---|
| 2009/0076584 A1* | 3/2009 | Mao | A61F 2/91 623/1.11 |
| 2012/0089238 A1 | 4/2012 | Kang et al. | |
| 2015/0076584 A1* | 3/2015 | Pachamuthu | H01L 29/66825 257/315 |
| 2015/0079584 A1* | 3/2015 | Gevaert | C12N 5/0062 435/6.1 |
| 2015/0377861 A1* | 12/2015 | Pant | C12M 25/14 506/9 |
| 2017/0307598 A1 | 10/2017 | Skardal et al. | |
| 2019/0106673 A1 | 4/2019 | Skardal | |

FOREIGN PATENT DOCUMENTS

| | | |
|---|---|---|
| JP | 2015510391 A | 4/2015 |
| JP | 2014033626 | 9/2015 |
| WO | 2005050200 A2 | 6/2005 |
| WO | 2013096741 A2 | 6/2013 |
| WO | 2015112624 | 7/2015 |
| WO | 2016/064648 | 4/2016 |
| WO | 2017059171 A1 | 4/2017 |
| WO | 2018027023 A1 | 2/2018 |
| WO | 2018071354 A1 | 4/2018 |
| WO | 2018071797 A1 | 4/2018 |
| WO | 2018081425 A1 | 5/2018 |
| WO | 2019028131 A1 | 2/2019 |
| WO | 2019152767 A1 | 8/2019 |

OTHER PUBLICATIONS

Amirabadi et al. "Cancer metastasis-on-a-chip" *Poster session presented at conference; Mate Poster Award 2013: 18th Annual Poster Contest* (2 pages) (Jan. 1, 2013).
International Search Report and the Written Opinion of the International Searching Authority corresponding to International Patent Application No. PCT/US2016/054611 (10 pages) (dated Dec. 9, 2016).
Skardal et al. "Liver-Tumor Hybrid Organoids for Modeling Tumor Growth and Drug Response In Vitro" *Annual Review of Biomedical Engineering* 43(10):2361-2373 (2015).
Extended European Search Report corresponding to European Patent Application No. 16852659.8 (7 pages) (dated Mar. 7, 2019).
Sung et al. "A micro cell culture analog (µCCA) with 3-D hydrogel culture of multiple cell lines to assess metabolism-dependent cytotoxicity of anti-cancer drugs" Lab on a Chip, 9:1385-1394 (2009).
Sung et al. "A microfluidic device for a pharmacokinetic-pharmacodynamics (PK-PD) model on a chip" Lab on a Chip, 10:446-455 (2010).
Allison et al. "Review. Hyaluronan: a powerful tissue engineering tool" Tissue Engineering, 12(8):2131-2140 (2006).
Batchelder et al. "Three Dimensional Culture of Human Renal Cell Carcinoma Organoids" PLoS ONE, 10(8): (2015) e0136758.
Behrens, J. "Control of beta-catenin signaling in tumor development" Annals of the New York Academy of Sciences, 910:21-33; discussion pp. 33-25 (2000)

Benam et al. "Engineered In Vitro Disease Models" Annual Review of Pathology: Mechanisms of Disease, 10:195-262 (2015).
Bersini et al. "A Microfluidic 3D In Vitro Model for Specificity of Breast Cancer Metastasis to Bone" Biomaterials, 35 (8):2454-2461 (2014).
Brantjes et al. "TCF: Lady Justice Casting the Final Verdict on the Outcome of Wnt Signalling" Biological Chemistry, 383(2):255-261 (2002).
Burdick et al. "Hyaluronic Acid Hydrogels for Biomedical Applications" Advanced Materials, 23(12):H41-H56 (2011).
Cantrell et al. "Organoid modeling for cancer precision medicine" Genome Medicine, 7(32):1-3 (2015).
Cirkel et al. "Tumor heterogeneity and personalized cancer medicine: are we being outnumbered?" Future Oncology, 10(3):417-428 (2014).
Clevers et al. "Q&A: Hans Clevers. Banking on organoids" Nature, 521(7551):S15 (2015).
Dedhia et al. "Organoid Models of Human Gastrointestinal Development and Disease" Gastroenterology, 150:1098-1112 (2016).
Devarasetty et al. "A Metastasis-on-a-Chip System for Modeling Colon Carcinoma Migration and Invasion in Vitro" Tissue Engineering: Part A, 20(Supplement 1):S-15 Oral Abstract O-182 (2 pages) (2014 TERMIS-AM Conference, Washington, DC, Dec. 13-16, 2014).
Devarasetty et al. "Modeling the Colon-Tumor Microenvironment Using Multicellular Hydrogel Strata" Tissue Engineering: Part A, 20(Supplement 1):S-77 Poster Abstract P-241 (2 pages) (2014 TERMIS-AM Conference, Washington, DC, Dec. 13-16, 2014).
Drewitz et al. "Towards automated production and drug sensitivity testing using scaffold-free spherical tumor microtissues" Biotechnology Journal, 6(12):1488-1496 (2011).
Fidler et al. "The role of the organ microenvironment in the biology and therapy of cancer metastasis" Journal of Cellular Biochemistry, 101:927-936 (2007).
Franci et al. "Biomarkers of Residual Disease, Disseminated Tumor Cells, and Metastases in the MMTV-PyMT Breast Cancer Model" PLoS One, 8:e58183 (2013).
Francies et al. "What role could organoids play in the personalization of cancer treatment?" Pharmacogenomics, 16 (14):1523-1526 (2015).
Fu et al. "A microfluidic chip with a U-shaped microstructure array for multicellular spheroid formation, culturing and analysis" Biofabrication, 6:1-9 (2014).
Gao et al. "Organoid Cultures Derived from Patients with Advanced Prostate Cancer" Cell, 159:176-187 (2014).
Gavert et al. "Coordinating changes in cell adhesion and phenotype during EMT-like processes in cancer" F1000 Reports Biology, 2(86):1-4 (2010).
Ho et al. "Incorporation of multicellular spheroids into 3-D polymeric scaffolds provides an improved tumor model for screening anticancer drugs" Cancer Science, 101:2637-2643 (2010).
Huang et al. "Ductal pancreatic cancer modeling and drug screening using human pluripotent stem cell- and patient-derived tumor organoids" Nature Medicine, 21:1364-1371 (2015).
Ikpa et al. "Cystic fibrosis: toward personalized therapies" The International Journal of Biochemistry & Cell Biology, 52:192-200 (2014).
Karakiulakis et al. "Increased type IV collagen-degrading activity in metastases originating from primary tumors of the human colon" Invasion & Metastasis, 17(3):158-168 (1997).
Kunz-Schughart et al. "The Use of 3-D Cultures for High-Throughput Screening: The Multicellular Spheroid Model" Journal of Biomolecular Screening, 9(4):273-285 (2004).
Lang et al. "Three-dimensional culture of hepatocytes on porcine liver tissue-derived extracellular matrix" Biomaterials, 32(29):7042-7052 (2011).
Langley et al. "Tumor Cell-Organ Microenvironment Interactions in the Pathogenesis of Cancer Metastasis" Endocrine Reviews, 28:297-321 (2007).
Levental et al. "Matrix Crosslinking Forces Tumor Progression by Enhancing Integrin signaling" Cell, 139:891-906 (2009).

(56) References Cited

OTHER PUBLICATIONS

McGrail et al. "Snail-induced epithelial-to-mesenchymal transition produces concerted biophysical changes from altered cytoskeletal gene expression" The FASEB Journal, 29:1280-1289 (2015).
Mou et al. "Personalized Medicine for Cystic Fibrosis: Establishing Human Model Systems" Pediatric Pulmonology, 50:S14-S23 (2015).
Murphy et al. "Evaluation of hydrogels for bio-printing applications" Journal of Biomedical Materials Research Part A, 101(1):272-284 (2013).
Nantasanti et al. "Concise Review: Organoids Are a Powerful Tool for the Study of Liver Disease and Personalized Treatment Design in Humans and Animals" Stem Cells Translational Medicine, 5:325-330 (2016).
Oleaga et al. "Multi-Organ toxicity demonstration in a functional human in vitro system composed of four organs" Scientific Reports, 6(20030):1-17 (2016).
Orsulic et al. "E-cadherin binding prevents beta-catenin nuclear localization and beta-catenin/LEF-1-mediated transactivation" Journal of Cell Science, 112:1237-1245 (1999).
Polini et al. "Organs-on-a-chip: a new tool for drug discovery" Expert Opinion on Drug Discovery, 9(4):335-352 (2014).
Prestwich, Glenn D. "Simplifying the extracellular matrix for 3-D cell culture and tissue engineering: A pragmatic approach" Journal of Cellular Biochemistry, 101(6):1370-1383 (2007).
Prestwich et al. "Chemically-modified HA for therapy and regenerative medicine" Current Pharmaceutical Biotechnology, 9(4):242-245 (2008).
Prestwich, Glenn D. "Evaluating Drug Efficacy and Toxicology in Three Dimensions: Using Synthetic Extracellular Matrices in Drug Discovery" Accounts of Chemical Research, 41(1):139-148 (2008).
Prestwich, Glenn D. "Hyaluronic Acid-Based Clinical Biomaterials Derived for Cell and Molecule Delivery in Regenerative Medicine" Journal of Controlled Release, 155:193-199 (2011).
Sachs et al. "Organoid cultures for the analysis of cancer phenotypes" Current Opinion in Genetics & Development, (2014) 24:68-73.
Schwarz et al. "Value of Organoids from Comparative Epithelia Models" Yale Journal of Biology and Medicine, (2015) 88:367-374.
Shin et al. "Microfluidic assay for simultaneous culture of multiple cell types on surfaces or within hydrogels" Nature Protocols, 7(7):1247-1259 (2014).
Skardal et al. "Bioprinting vessel-like constructs using hyaluronan hydrogels crosslinked with tetrahedral polyethylene glycol tetracrylates" Biomaterials, 31:6173-6181 (2010).
Skardal et al. "Dynamically Crosslinked Gold Nanoparticle—Hyaluronan Hydrogels" Advanced Materials, 22:4736-4740 (2010).
Skardal et al. "Photocrosslinkable Hyaluronan-Gelatin Hydrogels for Two-Step Bioprinting" Tissue Engineering: Part A, 16(8):2675-2685 (2010).
Skardal et al. "Tissue specific synthetic ECM hydrogels for 3-D in vitro maintenance of hepatocyte function" Biomaterials, 33(18):4565-4575 (2012).
Skardal et al. "An In Vitro 3-D Liver-Tumor Hybrid Organoid System for Modeling Metastasis and Drug Resistance" Tissue Engineering: Part A, 20(Supplement 1):S-15 Oral Abstract O-180 (2 pages) (2014 TERMIS-AM Conference, Washington, DC, Dec. 13-16, 2014).
Skardal et al. "Integration of 3-D Organoid Bioprinting and Microfluidic Device Technology for Functional Primary Cell-Based Liver-on-a-Chip Operation" Tissue Engineering: Part A, 20(Supplement 1):S-43 Oral Abstract O-527 (2 pages) (2014 TERMIS-AM Conference, Washington, DC, Dec. 13-16, 2014).
Skardal et al. "A Microfluidic Platform for Parallel Analysis of In Situ Patterned 3-D Liver Organoids" Tissue Engineering: Part A, 20(Supplement 1):S-68-S-69, Poster Abstract P-183 (3 pages) (2014 TERMIS-AM Conference, Washington, DC, Dec. 13-16, 2014).
Skardal et al. "Biomaterials for integration with 3-d bioprinting" Annals of Biomedical Engineering, 43(3):730-746 (2015).
Skardal et al. "In situ patterned micro 3D liver constructs for parallel toxicology testing in a fluidic device" Biofabrication, 7(3):031003 (pp. 1-16) (2015).
Skardal et al. "A Reductionist Metastasis-on-a-Chip Platform for In Vitro Tumor Progression Modeling and Drug Screening" Biotechnology and Bioengineering, 113(9):2020-2032 (2016).
Stock et al. "Targets for Anti-metastatic Drug Development" Current Pharmaceutical Design, 19(28):5127-5134 (2013).
Tania et al. "Epithelial to mesenchymal transition inducing transcription factors and metastatic cancer" Tumour biology: the Journal of the International Society for Oncodevelopmental Biology and Medicine, 35(8):7335-7342 (2014).
Van De Stolpe et al. "Workshop meeting report Organs-on-Chips: human disease models" Lab Chip, 13 (18):3449-3470 (2013).
Weeber et al. "Preserved genetic diversity in organoids cultured from biopsies of human colorectal cancer metastases" Proceedings of the National Academy of Sciences USA, 112(43):13308-13311 (2015).
Xia et al. "Soft Lithography" Annual Review of Materials Science, 28:153-184 (1998).
Zaman et al. "Migration of tumor cells in 3D matrices is governed by matrix stiffness along with cell-matrix adhesion and proteolysis" Proceedings of the National Academy of Sciences USA, 103(29):10889-10894 (2006).
Zhang et al. "Engineered Extracellular Matrices with Cleavable Crosslinkers for Cell Expansion and Easy Cell Recovery" Biomaterials, 29(34):4521-4531 (2008).
Zhang et al. "Personalizing pancreatic cancer organoids with hPSCs" Nature Medicine, 21:1249-1251 (2015).
Li et al. "Microfluidic 3D cell culture: potential application for tissue-based bioassays" Bioanalysis, 4(12):1509-1525 (2012).
Tehranirokh et al. "Microfluidic devices for cell cultivation and proliferation" Biomicrofluidics, 7:051502-1-051502-32 (2013).
Van Duinen et al. "Microfluidic 3D cell culture: from tools to tissue models" Current Opinion in Biotechnology, 35:118-126 (2015).
Zhang et al. "Towards a human-on-chip: Culturing multiple cell types on a chip with compartmentalized microenvironments" Lab on a Chip, 22:3185-3192 (2009) (Abstract only).

\* cited by examiner

I) Linear PEGDA     E' ~100 Pa

II) 4-Arm PEG-Acrylate     E' ~2 kPa

III) 8-Arm PEG-Acrylate     E' 4–5 kPa

METHODS AND APPARATUS FOR MODELING CANCER METASTASIS IN VITRO

RELATED APPLICATIONS

This application claims the benefit of U.S. Provisional Patent Application Ser. No. 62/236,361, filed Oct. 2, 2015, and of U.S. Provisional Patent Application Ser. No. 62/241,872, the disclosures of both of which are incorporated by reference herein in their entirety.

FIELD OF THE INVENTION

The present invention concerns methods and apparatus useful for studying the spread of cancer in vitro, including the effects of potential therapeutic compounds thereon.

BACKGROUND OF THE INVENTION

Despite advances in medical treatments, cancer metastasis is still not well understood, in particular: i) the mechanisms behind activation of tumor cell growth and malignancy, ii) how these mechanisms impact the logistics and kinetics of metastasis, and iii) the role that the microenvironment plays in regulating these phenomena.[1,2] While cancer research continues to progress, in recent years it has been limited due to the inability to accurately model tumor progression and metastasis in a controlled environment. Animal models allow only limited manipulation and study of the mechanisms at play, and are not necessarily predictive of results in humans. On the other hand, in vitro methods, such as traditional 2-D cultures, fail to recapitulate the 3-D microenvironment of in vivo tissues.[3] Drug diffusion kinetics vary dramatically, drug doses effective in 2-D are often ineffective when scaled to patients, cellular phenotypes can differ, and cell-cell/cell-matrix interactions are inaccurately modeled.[4-6] These limitations result in "top level" drug candidates often reaching clinical trials and failing because they have not been tested in accurate human-based models.

SUMMARY OF THE INVENTION

Platforms that include 3-D tissue constructs, or organoids, created using 3-D biomaterial systems and human (or other mammalian) derived cells offer a better solution for mimicking native physiology, modeling diseases, and performing drug screening.[7,8]

Our laboratory has extensive experience with fabrication and maintenance of tissue constructs of various types, including liver and intestine, and has been a part of the development and implementation of a number of hydrogel technologies to do so.[9-15] These types of approaches to hydrogel biofabrication, which in some embodiments may utilize hyaluornic acid hydrogels,[16-20] can be used to create engineered 3-D mammalian-specific models that can more accurately recapitulate mammalian physiology and disease.

In the case of metastasis research, there is a lack of in vitro models that distinguish between the primary tumors and the distant metastatic growth. Here we describe the initial implementation of multiple 3-D organoids within a closed fluidic system that allows control over the environment and investigation of mechanisms of metastasis at play across two distinct tissues in one platform—a "metastasis-on-a-chip" (MOC). The introduction of tumor foci within host tissue constructs is a concept that to date has not been sufficiently employed. This nexus of tissue engineering with small or micro-scale devices, paired with potential for real time live imaging, results in a powerful investigative and diagnostic tool. By providing flow through the fluidic device organoid system, we can study the dissemination of colon carcinoma cells from the gut organoid into circulation, after which metastatic cells can attach and invade the liver organoid downstream. The microfluidic model is one of the first in vitro models of metastasis recapitulating migration from a 3-D originating tissue to a 3-D target tissue. This is notable because the phenotype of cells in the originating malignant tumors and metastases can vary significantly—for example, resulting in varying levels of invasiveness due to matrix metalloproteinase (MMP) secretion and stem cell-like gene expression[21,22]—making the ability to study tumors in various settings, their microenvironments, and during migration extremely informative.

A first aspect of the invention is, accordingly, an apparatus useful for examining metastasis of cancer cells, comprising:
(a) a primary chamber;
(b) at least one secondary chamber;
(c) at least one primary conduit connecting the primary and secondary chambers and providing fluid communication (e.g., such as the flow of a growth media) therebetween;
(d) a primary organoid in the first chamber, the primary organoid comprising mammalian cancer cells;
(e) at least one secondary organoid in each the secondary chamber; and
(f) optionally a growth media in the primary chamber, each secondary chamber, and the primary conduit.

In some embodiments, the apparatus further includes an optically transparent window in the primary and/or secondary chambers, as discussed further below.

In some embodiments, the apparatus further includes a fluid inlet connected to the primary chamber and a fluid outlet connected to each secondary chamber.

In some embodiments, the cancer cells express a detectable compound.

In some embodiments of the foregoing, the first organoid further includes: (i) mammalian tissue cells, optionally in an extracellular matrix; or (ii) an extracellular matrix carrying the cancer cells; and (iii) optionally, a layer of blood vessel or lymphatic endothelial cells at least partially around or above the first organoid (e.g., to serve as a representation of the endothelial barrier that cancer cells must penetrate to enter circulation); and (iv) optionally, immune system cells (e.g., as Kupffer cells, macrophages, monocytes, neutrophils, etc.).

A further aspect of the invention is a method of screening a test compound for anti-metastatic (or other physiological or pharmacological) activity against cancer cells, comprising the steps of:
(a) providing an apparatus as described herein;
(b) circulating a growth medium from the first chamber to the second chamber;
(c) administering a test compound to the first organoid (e.g., by adding the test compound to the growth medium); and
(d) determining a decrease in the presence of cancer cells (change in number or density) in the second organoid, as compared to the number of cancer cells present in the second organoid when the test compound is not administered.

The present invention is explained in greater detail in the drawings herein and the specification set forth below. The disclosures of all United States Patent references cited herein are to be incorporated by reference herein in their entirety.

DETAILED DESCRIPTION OF THE PREFERRED EMBODIMENTS

Figure 1A:
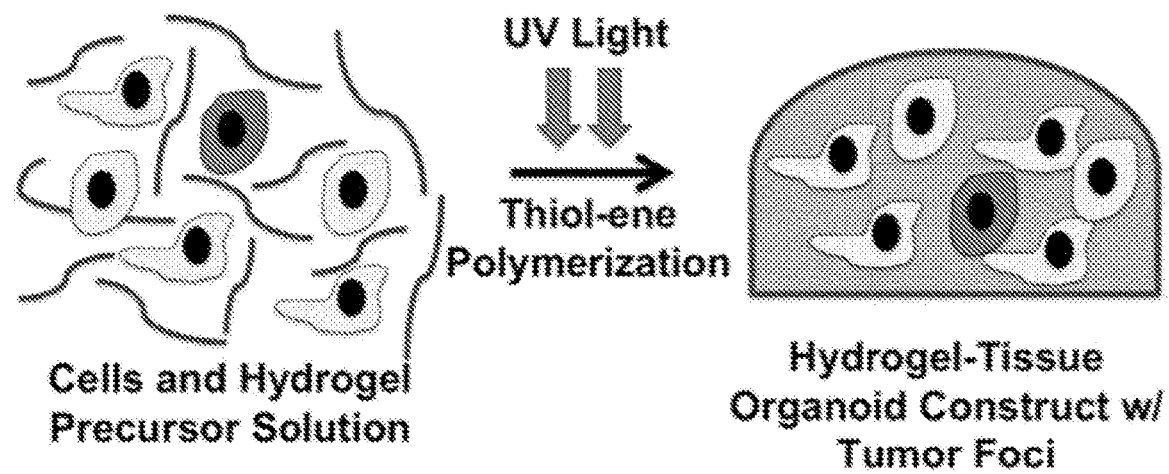
FIG. 1A. The 2-organoid "metastasis-on-a-chip" device and fluidic platform for mimicking colon carcinoma metastasis from the gut to the liver. Photopolymerization of cells in a polymer solution forms 3-D tissue constructs.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

A. Definitions

"Cells" used in the present invention are, in general, animal cells, particularly mammalian and primate cells, examples of which include but are not limited to human, dog, cat, rabbit, monkey, chimpanzee, cow, pig, goat. In some embodiments, the cells are obtained from a subject or patient undergoing treatment for cancer. The cells are preferably differentiated at least in part to a particular cell or tissue type, such as liver, intestine, pancreas, lymph node, smooth muscle, skeletal muscle, central nerve, peripheral nerve, skin, immune system, etc. Some cells may be cancer cells, as discussed further below, in which case they optionally but preferably express (naturally, or by recombinant techniques) a detectable compound, as also discussed further below.

"Organoid" is used interchangeably with "three dimensional tissue construct" herein, and refers to a composition of live cells, typically in a carrier media, arranged in a three-dimensional or multi-layered configuration (as opposed to a monolayer). Suitable carrier media include hydrogels, such as cross-linked hydrogels as described below. Organoids may comprise one differentiated cell type, or two or more differentiated cell types, depending upon the particular tissue or organ being modeled or emulated. Some organoids may comprise cancer cells, as discussed further below. Where organoids comprise cancer cells, they may include tissue cells, and/or may include a tissue mimic without cells, such as an extracellular matrix (or proteins or polymers derived therefrom), hyaluronic acid, gelatin, collagen, alginate, etc., including combinations thereof. Thus in some embodiments, cells are mixed together with the extracellular matrix, or cross-linked matrix, to form the organoid or construct, while in other embodiments cell aggregates such as spheroids or organoids may be pre-formed and then combined with the extracellular matrix.

"Growth media" as used herein may be any natural or artificial growth media (typically an aqueous liquid) that sustains the cells used in carrying out the present invention. Examples include, but are not limited to, an essential media or minimal essential media (MEM), or variations thereof such as Eagle's minimal essential medium (EMEM) and Dulbecco's modified Eagle medium (DMEM), as well as blood, blood serum, blood plasma, lymph fluid, etc., including synthetic mimics thereof. In some embodiments, the growth media includes a pH color indicator (e.g., phenol red).

"Test compound" or "candidate compound" as used herein may be any compound for which activity in inhibiting the spreading of cancer cells from a primary site to a second site is to be determined. For demonstrative purposes, Marimastat (N-[2,2-dimethyl-1-(methylcarbamoyl)propyl]-2-[hydroxy-(hydroxycarbamoyl)methyl]-4-methyl-pentanamide) is used as a test compound. However, any compound may be used, typically organic compounds such as proteins, peptides, nucleic acids, and small organic compounds (aliphatic, aromatic, and mixed aliphatic/aromatic compounds) may be used. Candidate compounds may be generated by any suitable techniques, including randomly generated by combinatorial techniques, and/or rationally designed based on particular targets. See, e.g., A. M. Stock et al., *Targets for anti-metastatic drug development*, Curr. Pharm. Des. 19(28): 5127-34 (2013).

"Detectable compound" as used herein may be a fluorescent protein (e.g., red fluorescent protein, green fluorescent protein, etc.), an antigenic protein or peptide to which an antibody coupled to an enzyme, fluorescent, or radioactive group, or other label, will specifically bind), or any other suitable detectable compound. The detectable compound may be one naturally occurring in a cancer cell (e.g., a cell marker protein that is expressed at higher levels in cancer cells than non-cancer cells), or one inserted into cancer cells by genetic engineering/recombinant DNA techniques (i.e., heterologous).

B. Compositions

Compositions of the present invention may comprise live cells in a "bioink," where the "bioink" is in turn comprised of a cross-linkable polymer, a post-deposition crosslinking group or agent; and other optional ingredients, including but not limited to growth factors, initiators (e.g., of cross-linking), water (to balance), etc. The compositions are preferably in the form of a hydrogel. Various components and properties of the compositions are discussed further below.

Cells.

As noted above, cells used to carry out the present invention are preferably animal cells (e.g., bird, reptile, amphibian, etc.) and in some embodiments are preferably mammalian cells (e.g., dog, cat, mouse, rat, monkey, ape, human). The cells may be differentiated or undifferentiated cells, but are in some embodiments tissue cells (e.g., liver cells such as hepatocytes, pancreatic cells, cardiac muscle cells, skeletal muscle cells, etc.). Also as noted above, in some embodiments, the cells are obtained from a subject or patient undergoing treatment for cancer.

Choice of cells will depend upon the particular organoid being created. For example, for a liver organoid, liver hepatocyte cells may be used. For a peripheral or central nerve organoid, peripheral nerve cells, central nerve cells, glia cells, or combinations thereof may be used. For a bone organoid, bone osteoblast cells, bone osteoclast cells, or combinations thereof may be used. For a lung organoid, lung airway epithelial cells may be used. For a lymph node organoid, follicular dendritic lymph cells, fibroblastic reticular lymph cells, leucocytes, B cells, T cells, or combinations thereof may be used. For a smooth or skeletal muscle organoid, smooth muscle cells, skeletal muscle cells, or combinations thereof may be used. For a skin organoid, skin keratinocytes, skin melanocytes, or combinations thereof may be used.

The cells may be differentiated upon initial incorporation into the composition, or undifferentiated cells that are subsequently differentiated may be used. Cells collected from a patient may be de-differentiated and re-differentiated as needed. Additional cells may be added to any of the compositions described above, and cancer cells as described below may be added to primary or "first" organoids, as described below.

Cancer cells used in the present invention may be any type of cancer cell, including but not limited to melanoma, carcinoma, sarcoma, blastoma, glioma, and astrocytoma cells, etc. In some embodiments, the cancer cells used in the present invention express N-cadherin in the methods taught herein, and/or show epithelial to mesenchymal transition.

Thus, by choosing different combinations of cells for the compositions deposited in each chamber to form the various organoids, the invention may be implemented in a manner that serves as a model system for any of a variety of cancers and their metastasis. Non-limiting examples of different combinations of cells include the cases where:

(i) the first organoid comprises intestinal epithelial cells in combination with colon carcinoma cells, and the second organoid comprises a liver, central nerve, peripheral nerve, or bone organoid;

(ii) the first organoid comprises lung airway epithelial cells in combination with either small cell lung cancer or lung adenocarcinoma cells, and the second organoid comprises a pheripheral nerve, central nerve, liver, or bone organoid;

(iii) the first organoid comprises mammary gland epithelial cells in combination with breast carcinoma, adenocarcinoma or sarcoma cells, and the second organoid comprises a liver, peripheral nerve, central nerve (e.g., brain tissue), bone, lung, lymph node, smooth muscle, skeletal muscle, or skin organoid;

(iv) the first organoid comprises prostate gland cells in combination with prostate acinar or ductal adenocarcinoma cells, and the second organoid comprises a liver, peripheral nerve, central nerve, bone, lung, or lymph node organoid;

(v) the first organoid comprises keratinocytes, optionally melanocytes, and melanoma cells in combination, and the second organoid comprises a liver, peripheral nerve, central nerve, bone, lung, skin or lymph node organoid.

(vi) the first organoid comprises central nervous system tumor cells (e.g., glioblastoma cells, astrocytoma cells, etc.) optionally differentiated central nervous system cells (e.g., astrocytes, neurons, etc.) and the second organoid comprises a central nerve organoid;

(vii) the first organoid comprises liver cells in combination with hepatoma or hepatocellular carcinoma cells, and the second organoid comprises a pheripheral nerve, central nerve, lymph node, lung, or bone organoid;

(viii) the first organoid comprises pancreatic cells in combination with pancreatic adenocarcinoma cells, and the second organoid comprises a pheripheral nerve, central nerve, lymph node, liver, lung, or bone organoid;

(ix) the first organoid comprises uterine endometrial cells, and optionally myometrial cells, in combination with endometrial carcinoma, uterine sarcoma, or uterine carcinosarcoma cells, and the second organoid comprises a lung, lymph node, liver, bone, central nerve, skin, smooth muscle, or skeletal muscle organoid; or (x) the first organoid comprises cervical mucosa cells and optionally smooth muscle cells in combination with cervical squamous carcinoma or adenocarcinoma cells, and the second organoid comprises bladder, bone, lung, liver, smooth muscle, skeletal muscle, or intestinal organoid.

The cells may be incorporated into the composition in any suitable form, including as unencapsulated cells, or as cells previously encapsulated in spheroids, or pre-formed organoids (as noted above). Animal tissue cells encapsulated or contained in polymer spheroids can be produced in accordance with known techniques, or in some cases are commercially available (see, e.g., Insphero AG, 3D Hepg2 Liver Microtissue Spheroids (2012); Insphero AG, 3D InSight™ Human Liver Microtissues, (2012)).

Cross-Linkable Prepolymers.

Any suitable prepolymer can be used to carry out the present invention, so long as it can be further cross-linked to increase the elastic modulus thereof after deposition when employed in the methods described herein.

In some embodiments, the prepolymer is formed from the at least partial crosslinking reaction of: (1) an oligosaccharide (e.g., hyaluronic acid, collagen, combinations thereof and particularly thiol-substituted derivatives thereof) and (ii) a first crosslinking agent (e.g., a thiol-reactive crosslinking agent, such as polyalkylene glycol diacrylate, polyalkylene glycol methacrylate, etc., and particularly polyethylene glycol diacrylate, etc.; thiolated crosslinking agent to create thiol-thiol disulfide bonds; gold nanoparticles gold functionalized crosslinkers forming thiol-gold bonds; etc., including combinations thereof).

Cross-Linking Group.

In some embodiments, the compositions include a post-deposition crosslinking group. Any suitable crosslinking groups can be used, including but not limited to multi-arm thiol-reactive crosslinking agent, such as polyethylene glycol dialkyne, other alkyne-functionalized groups, acrylate or methacrylate groups, etc., including combinations thereof.

Initiators.

Compositions of the invention may optionally, but in some embodiments preferably, include an initiator (e.g., a thermal or photoinitiator). Any suitable initiator that catalyzes the reaction between said prepolymer and the second (or post-deposition) crosslinking group (e.g., upon heating or upon exposure to light), may be employed.

Growth Factors.

Compositions of the invention may optionally, but in some embodiments preferably, include at least one growth factor (e.g., appropriate for the particular cells included, and/or for the particular tissue substitute being produced). In some embodiments, growth factors and/or other growth promoting proteins may be provided in a decellularized extracellular matrix composition ("ECM") from a tissue corresponding to the tissue cells (e.g., decellularized extracellular liver matrix when the live animal cells are liver cells; decellularized extracellular cardiac muscle matrix when the live animal cells are cardiac muscle cells; decellularized skeletal muscle matrix when the live animal cells are skeletal muscle cells; etc.). Additional collagens, glycosaminoglycans, and/or elastin (e.g., which may be added to supplement the extracellular matrix composition), etc., may also be included.

Elastic Modulus.

The composition preferably has an elastic modulus, at room temperature and atmospheric pressure, sufficiently low such that it can be manipulated and deposited on a substrate by whatever deposition method is employed (e.g., extrusion deposition). Further, the composition optionally, but in some embodiments preferably, has an elastic modulus, again at room temperature and atmospheric pressure, sufficiently high so that it will substantially retain the shape or configuration in which it is deposited until subsequent cross-linking (whether that cross-linking be spontaneous, thermal or photo-initiated, etc.). In some embodiments, the composition, prior to deposition, has a stiffness of from 0.05, 0.1 or 0.5 to 1, 5 or 10 kiloPascals, or more, at room temperature and atmospheric pressure.

B. Methods of Making Devices

In one non-limiting, but preferred, method of use, the compositions are used in a method of making an organoid as described herein. Such a method generally comprises the steps of:

(a) providing a reservoir containing an extrudable hydrogel composition as described above, then (b) depositing the hydrogel composition onto a substrate (e.g., by extrusion through a syringe); and then (c) cross-linking said prepolymer with said second crosslinking group by an amount sufficient to increase the stiffness of said hydrogel and form said three-dimensional organ construct (e.g., by heating the hydrogel, irradiating the hydrogel composition with light (e.g., ambient light, UV light), altering the pH of the hydrogel; etc.).

In some embodiments, the hydrogel composition containing cells is applied to the central region of a preformed 3D organoid substrate without the cells, resulting in distinct cell-containing zones (e.g., tumor cell-containing zones) inside of outer organoid zones.

The depositing step may be carried out with any suitable apparatus, including but not limited to that described in H.-W. Kang, S. J. Lee, A. Atala and J. J. Yoo, US Patent Application Pub. No. US 2012/0089238 (Apr. 12, 2012). In some embodiments, the depositing step is a patterned depositing step: That is, deposition is carried out so that the deposited composition is deposited in the form of a regular or irregular pattern, such as a regular or irregular lattice, grid, spiral, etc.

In some embodiments, the cross-linking step increases the stiffness of said hydrogel by from 1 or 5 to 10, 20 or 50 kiloPascals, or more, at room temperature and atmospheric pressure.

In some embodiments, the hydrogel has a stiffness after said cross-linking step (c) of from 1 or 5 to 10, 20 or 50 kiloPascals at room temperature and atmospheric pressure.

In some embodiments, the method further comprises the step of depositing a supporting polymer (e.g., poly-L-lactic acid, poly(glycolic acid), polycaprolactone; polystyrene; polyethylene glycol, etc., including copolymers thereof such as poly(lactic-co-glycolic acid),) on said substrate in a position adjacent that of said hydrogel composition (e.g., concurrently with, after, or in alternating repetitions with, the step of depositing said hydrogel, and in some embodiments prior to the cross-linking step).

Any suitable substrate can be used for the deposition, including organic and inorganic substrates, and including substrates with or without features such as well, chambers, or channels formed thereon. For the particular products described herein, the substrate may comprise a microfluidic device having at least two chambers (the chambers optionally but preferably associated with an inlet channel and/or an outlet channel) connected by a primary fluid conduit through which the growth media may circulate, and the depositing is carried out separately in each chamber. In an alternative, the substrate may comprise a first and second planar member (e.g., a microscope cover slip), the depositing step may be carried out that planar member, and the method may further comprise the step of inserting each planar member into a separate chamber of a microfluidic device. Post-processing steps, such as sealing of chambers, and maintaining the viability of cells, may be carried out in accordance with known techniques.

While the present invention is described primarily with reference to a single secondary chamber, it will be appreciated that multiple secondary chambers, with the same or different organoids, may be included on the substrate if desired. Thus the secondary chambers can be connected to one another, and the primary chamber, in any suitable configuration, including in series, in parallel, or in combinations thereof.

The substrate carrying the primary and secondary chambers, associated organoids, inlets, outlets, and conduits, may be provided in the form of an independent "cartridge" or subcombination that may be installed within a larger apparatus in combination with additional components for use. Thus, in some such larger apparatus embodiments, the apparatus further includes a pump operatively associated with the primary chamber for circulating the growth media from the primary chamber to the secondary chamber.

In some embodiments, the apparatus further includes a growth media reservoir and/or bubble trap operatively associated with the primary chamber.

In some embodiments, the apparatus further includes a return conduit operatively associated with the primary and secondary chambers (and the pump, and reservoir and/or bubble trap when present) for returning growth media circulated through the secondary chambers to the primary chamber.

C. Packaging, Storage and Shipping

Once produced, subcombination or "cartridge" devices as described above may be used immediately, or prepared for storage and/or transport.

To store and transport the product, a transient protective support media that is a flowable liquid at room temperature (e.g., 25° C.), but gels or solidifies at refrigerated temperatures (e.g., 4° C.), such as a gelatin mixed with water, may be added into the device to substantially or completely fill the chambers, and preferably also the associated conduits. Any inlet and outlet ports may be capped with a suitable capping element (e.g., a plug) or capping material (e.g., wax). The device may then be packaged together with a cooling element (e.g., ice, dry ice, a thermoelectric chiller, etc.) and all placed in a (preferably insulated) package.

Alternatively, to store and transport the product, a transient protective support media that is a flowable liquid at cooled temperature (e.g., 4° C.), but gels or solidifies at warmed temperatures such as room temperature (e.g., 20° C.) or body temperature (e.g., 37° C.), such as poly(N-isopropylacrylamide and poly(ethylene glycol) block copolymers, may be used.

Upon receipt, the end user simply removes the device from the associated package and cooling element, allows the temperature to rise or fall (depending on the choice of transient protective support media), uncaps any ports, and removes the transient protective support media with a syringe (e.g., by flushing with growth media).

D. Methods of Use

As noted above, a further aspect of the invention is a method of screening a test compound for anti-metastatic (or other physiological or pharmacological) activity against cancer cells, comprising the steps of:

(a) providing an apparatus as described herein;

(b) circulating a growth medium from the first chamber to the second chamber;

(c) administering a test compound to the first organoid (e.g., by adding the test compound to the growth medium); and (d) determining a decrease in the presence of cancer cells in the second organoid, as compared to the number of cancer cells present in the second organoid when the test compound is not administered.

When the cancer cells express a detectable compound, the second chamber can have an optically transparent window therein, as noted above, and the determining step can be carried out by detecting the detectable compound through the window. Alternatively, the apparatus can be disassembled at the end of the procedure and the organoids examined directly.

The determining step may be carried out on a single occasion, or a plurality of occasions at different times sequentially spaced from one another (e.g., at least two occasions spaced at least a day apart).

In some embodiments of the foregoing, the screening may include assessment of cellular metabolism, including metabolism of a particular test compound, or cellular toxicity induced by the cancer cells or by a particular test compound. The present invention is explained in greater detail in the following non-limiting examples.

EXPERIMENTAL

Materials and Methods
Cell Culture.

Human colon carcinoma cells (HCT-116, transfected previously with red fluorescent protein [RFP]), human intestine epithelial cells (INT-407), and human hepatoma cells (HepG2) were expanded in 2-D on tissue culture plastic using 15 cm tissue-treated dishes until 90% confluence with Dulbecco's Minimum Essential Medium (DMEM, Sigma, St. Louis, Mo.), containing 10% fetal bovine serum (FBS, Hyclone, Logan, Utah). Cells were detached from the substrate with Trypsin/EDTA (Hyclone) and resuspended in media before use in further studies.

Fluidic Device Fabrication and Fluid Circuit Operation.

Each device consists of 2 circular chambers (10 mm diameter, 3 mm thick), each accessible via its own fluidic channel with an individually addressable inlet and outlet. These structures are fabricated using conventional soft lithography, replica molding, and layer-by-layer stacking.[23] Briefly, inverted chamber/channel structures were produced with 3D printing (Zprinter 450, Z Corp., Rock Hill, S.C.) and used as molds. Polydimethylsiloxane (Sylgard 184, Dow Corning Corporation, Midland, Mich.) was mixed thoroughly with its curing agent and degassed under vacuum in a desiccation chamber before being poured directly on the mold and cured at 60° C. for 60 min. Following curing, the device was isolated from the unnecessary material using a razor and removed from the mold. After cleaning with ethanol, the layers of PDMS were stacked and ready for organoid integration. Following introduction of organoids, a flat piece of PDMS containing inlet and outlet ports was used to cover the chambers and channels and the whole device was sealed and clamped. Fluidic connections were made using stainless steel catheter couplers (Instech Laboratories, Plymouth Meeting, Pa.) and Sylastic tubing (Corning, Corning, N.Y.), which interfaced with the PDMS device through pre-fabricated accessible ports.

Hydrogel Organoid Formation.

Organoids were forming using a thiolated hyaluronic acid, thiolated gelatin, and polyethylene glycol diacrylate (PEGDA)-based hydrogel system (ESI-BIO, Alameda, Calif.). Thiolated HA and gelatin components were dissolved at 1% w/v each in water containing 0.1% w/v photoinitiator (2-Hydroxy-4'-(2-hydroxyethoxy)-2-methyl-propiophenone, Sigma, St. Louis, Mo.), and mixed with a 2% w/v linear polyethylene glycol diacrylate crosslinker solution in a 2:2:1 ratio by volume. For organoid formation, the hydrogel-precursor solution was used to resuspend cells at a cell density of $10 \times 10^6$ cells/mL. The primary site gut organoids containing colon carcinoma tumor foci were formed using Int-407 intestine epithelial cells and red fluorescent protein (RFP)-labeled HCT-116 colon carcinoma cells, combined in a 10:1 ratio by cell number. The secondary site liver organoids were formed using HepG2 liver cells only. Cell suspensions in the hydrogel precursors were pipetted in 25 µL aliquots into the appropriate device chambers, after which construct photopolymerization was achieved using exposure to UV light. Experiments were conducted using DMEM as described above.

Metastasis-On-a-Chip Culture.

Dual organoid culture onboard the MOC devices was performed after organoids had been formed in each of the device chambers, and the device pieces were sealed and clamped together. Sylastic tubing was used to connect MOCs, media reservoirs, and bubble traps to a MP2 Precision micro-peristaltic pump (Elemental Scientific, Inc., Omaha, Nebr.). Additional tubing further connects the pump to the device and back to the reservoirs, forming multiple closed parallel circuits. At the start of culture, 4 mL of media (DMEM) was placed in each reservoir after which fluid flow was initiated by the micro-peristaltic pump. Media flow was initiated and maintained at a rate of 5 µL/min throughout the experiment. Devices were operated continuously, with media changes occurring if the pH level of the media reservoir dropped, indicated by the phenol red component in the media. During media changes, spent media was removed from the system, placed into a conical tube, and centrifuged to avoid losing any tumor cells that might have entered circulation. Spent media was aspirated and replaced with fresh DMEM. The conical tubes were treated as if there was a cell pellet present—resuspension by pipetting media up and down—and this media and any cells present were returned to media reservoir. During MOC system culture, organoids and presence of fluorescent RFP-labeled tumor foci were documented over time by microscopy. Composite images were taken of the primary organoid on days 1, 4, 9, 11, 14, and 17, and secondary site following primary organoid tumor cell dissemination on days 14, 18, 20, and 24, in which the organoids were imaged with light microscopy and epifluorescence at 594 nm to analyze the progression of the RFP-labled HCT-116 cells within the non-fluorescent host liver organoids. Percentage of RFP-labeled HCT-116 tumor cell content was measured using a custom MatLab segmentation script. Subsets of organoids were fixed on day 21 for histological analysis.

Immunohistochemistry.

Organoids were fixed with 4% paraformaldehyde for 1 hour, dehydrated with graded ethanol washes followed by xylene, embedded in paraffin, and sectioned at 5 µm. For IHC, all incubations were carried out at room temperature unless otherwise stated. Slides were wainied at 60° C. for 1 hr to increase bonding to the slides. Antigen retrieval was performed on all slides and achieved with incubation in Proteinase K (Dako, Carpinteria, Calif.) for 5 min. Sections were permeabilized by incubation in 0.05% Triton-X for 5 min. Non-specific antibody binding was blocked by incubation in Protein Block Solution (Abeam) for 15 min. Sections were incubated for 60 min in a humidified chamber with the primary ZO-1 (raised in rabbit, cat. #61-7300, Invitrogen), β-catenin (raised in rabbit, cat. #71-2700, Invitrogen), vinculin (raised in mouse, cat. # V9264, Sigma Aldrich), N-cadherin (raised in mouse, 610921, BD Biosciences), and PCNA (raised in rabbit, cat. #07-2162, Millipore), all at 1:200 dilutions in antibody diluent (Abeam).

Following primary incubation, slides were washed 3 times in PBS for 5 min. Samples were then incubated for 1 hr with anti-rabbit, or anti-mouse Alexa Fluor 488 secondary antibodies (Invitrogen) as appropriate in antibody diluent (1:200 dilution).

Cells were counterstained with DAPI for 5 minutes, and washed 3 times with 1×PBS prior to fluorescent imaging. Negative controls were performed in parallel with the primary antibody incubations and included incubation with blocking solution in place of the primary antibody. No immunoreactivity was observed in the negative control sections. Samples were imaged by epifluorescence using excitation band filters with central excitation wavelengths 380 nm, 488 nm, and 594 nm with a Leica DM 4000B upright microscope (Leica Microsystems, Buffalo Grove, Ill.).

Organoid Environmental Stiffness Manipulation and Migration Tracking.

To assess the influence of the physical tumor microenvironment parameters on tumor cell migration, a variation of the organoids described above were faulted. Instead of encapsulating homogenously mixed cells throughout the hydrogel, 3-D organoid volumes were formed first, after which a volume of 5 µL HCT-116 cells in hydrogel precursor solution was pipetted into the center of the organoid space and polymerized in place by a 1 second exposure to UV light. This fabrication scheme resulted in outer organoid zones, inside of which distinct tumor zones resided. Organoid and tumor zone elastic moduli were modulated by swapping of the linear PEGDA crosslinker molecule (3.4 kDa MW) with a 4-arm PEG-acrylate molecule (10 kDa MW, Creative PEGWorks, Winston-Salem, N.C.) or 8-arm PEG-acrylate crosslinker molecule (10 kDa MW, Creative PEGWorks) to generate stiffer hydrogels. Organoid constructs were fabricated in 2 primary conditions: condition 1—stiff (8-arm crosslinker) HCT-116 tumor foci inside of a soft environment (linear crosslinker); or condition 2—soft (linear crosslinker) HCT-116 tumor foci inside of a stiff environment (8-arm crosslinker). Organoids were maintained as described above using DMEM. After 7 days, organoids were fixed, and are imaged using a Leica TCS LSI macro-confocal microscope. Z-stacks of 150 µm were taken of each construct near the top of the initial tumor zone, from which maximum projections (2-D compressed image) were obtained.

Drug Treatment and Assessment of Migration.

To investigate the likely mechanism of migration within the MOC system, and verify whether the tumor cells were susceptible to drug intervention, the effectiveness of the anti-matrix metalloproteinase drug Marimastat was tested using the multi-zone migration model described above. Tumor organoids were created once more, using the condition 2 described above (soft tumor, stiff tissue), in which, as described in the results, HCT-116 cells displayed heightened migration behavior. One half of the prepared systems received normal DMEM, while the other half received 50 µM Marimastat (Sigma) in DMEM. The drug-containing media was pHed to physiological pH to ensure that any pH changes due to the drug were not confounding results. Fluorescent and brightfield overlay images were captured on day 3, day 7, and day 10, from which distances of migration of cells out of the tumor were determined over time using ImageJ software.

Statistical Analysis.

The data are generally presented as the means of number of replicates±the standard deviation. All experiments were performed with n=3 or higher. Values were compared using Student's t-test (2-tailed) with two sample unequal variance, and $p<0.05$ or less was considered statistically significant.

Results

Tumor Organoids in the MOC System Migrate from Gut to Liver.

Figure 1B:
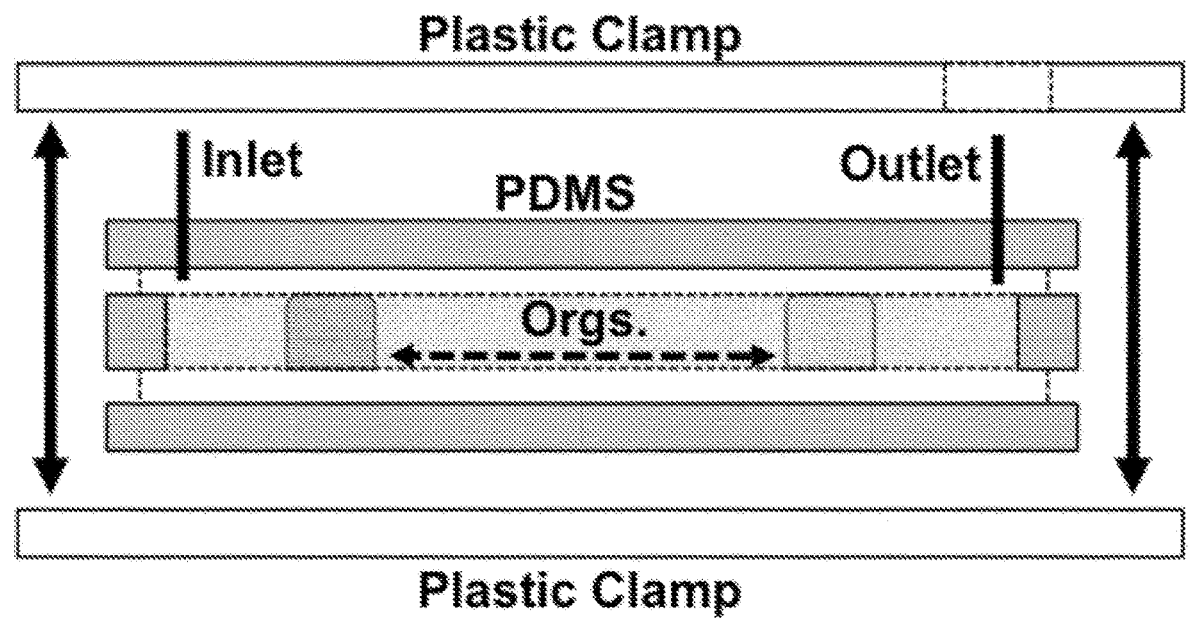
FIG. 1B. Device fabrication using molded PDMS pieces, inlet and outlet valves, and plastic clamps. Organoid placement ("Orgs.") is indicated by the blue and yellow zones.
Figure 1C:
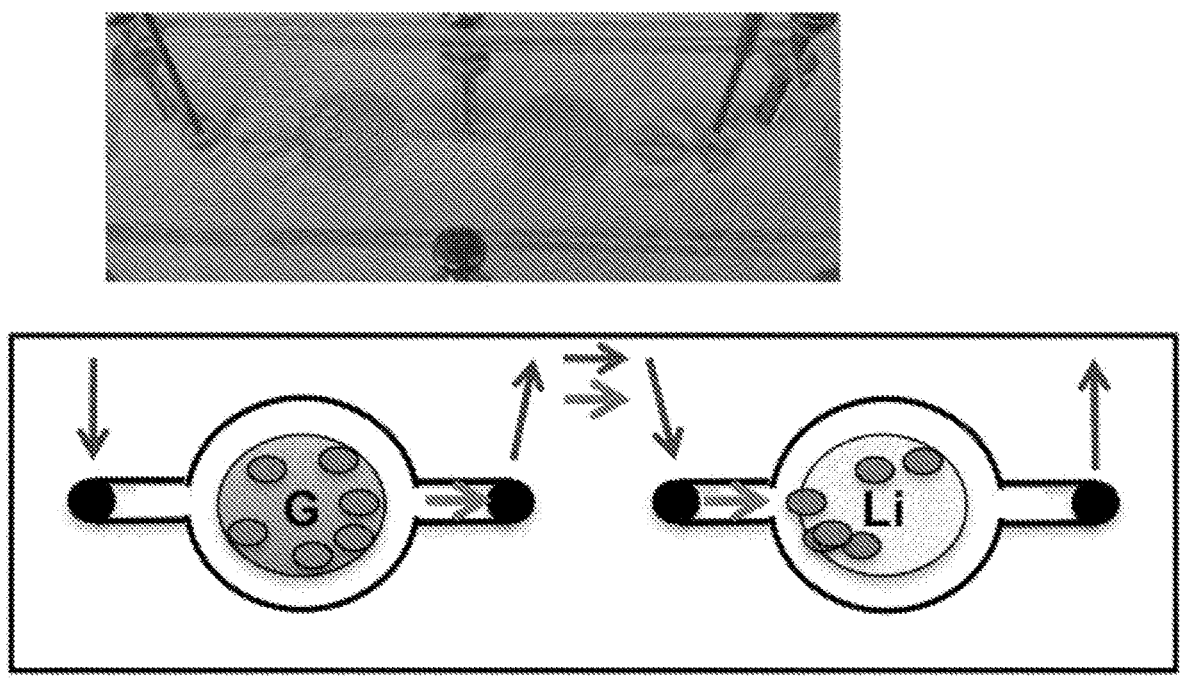
FIG. 1C. Photo and depiction of the device, and gut and liver constructs in the device under flow with migrating cancer cells.
Figure 1D:
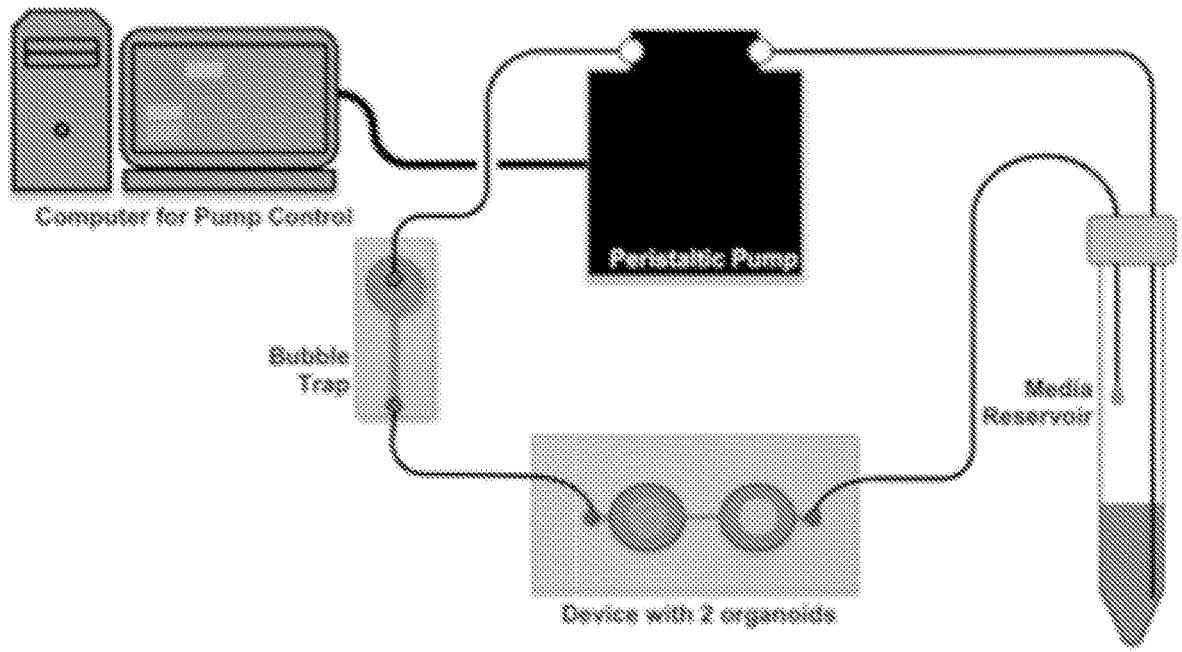
FIG. 1D. The MOC device inline with media reservoir, bubble trap, and micro-peristaltic pump, providing circulatory flow in the gut-to-liver direction.
Figures 2A, 2B:
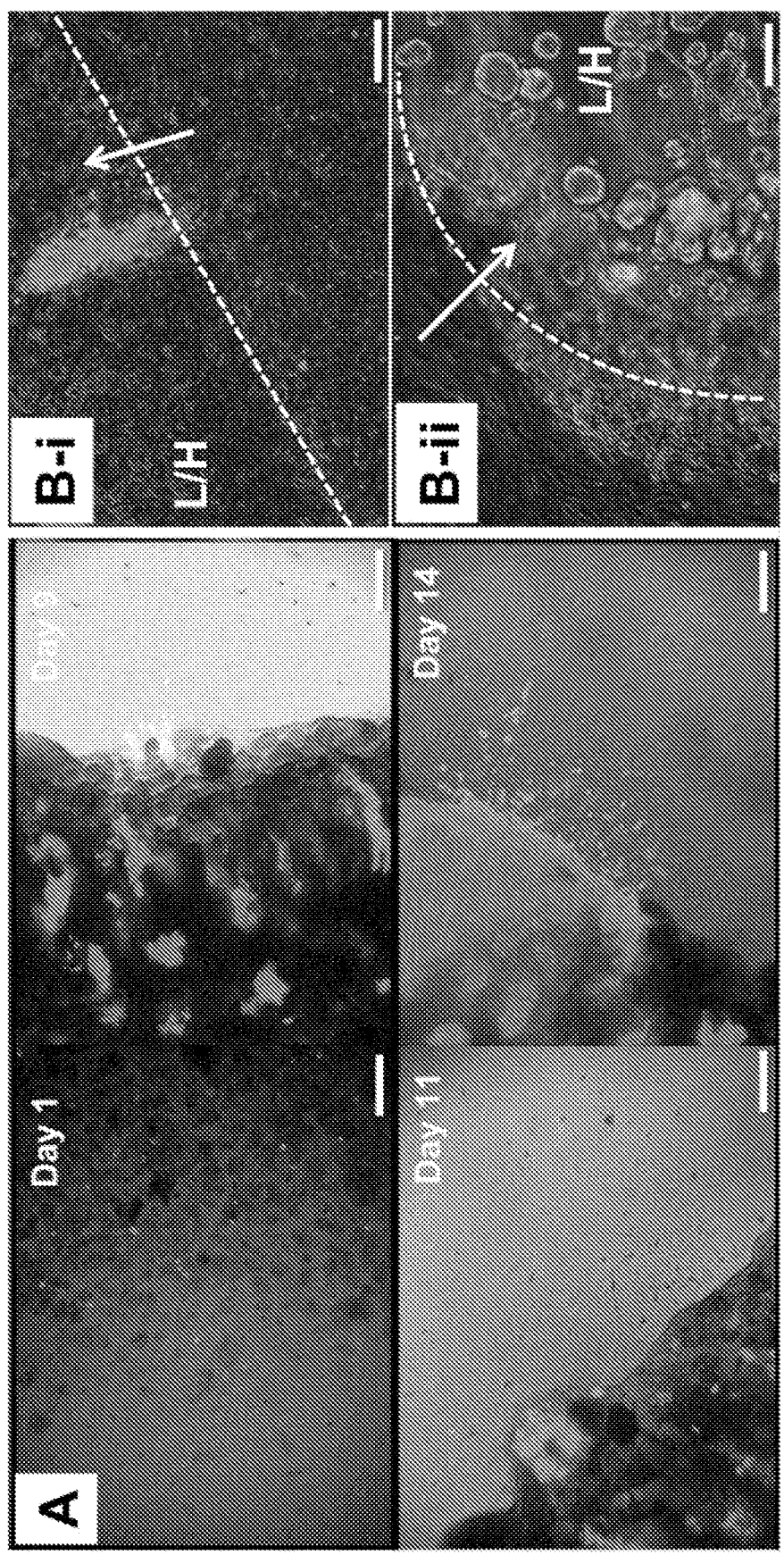
FIG. 2. Colon carcinoma metastasizes from the gut to the liver. A) Growth of HCT-116 cells in the primary construct, and subsequent shedding of RFP-labeled HCT-116 cells into circulation. B)(i-ii) Invasion of RFP-labeled HCT116 cells into liver organoids, via multicellular protrusions and aggregates invading a liver-hydrogel organoid. (Arrow—direction of invasion; Dotted line—organoid interface; L/H—liver/hydrogel construct). Scale bars—250 µm. organoid interface; L/H—liver/hydrogel construct). Scale bars—250 µm. C) Quantification of percentage RFP-stained HCT-116 tumor area within composite organoid images over time in the origin site and the downstream metastatic site.
Figure 2C:
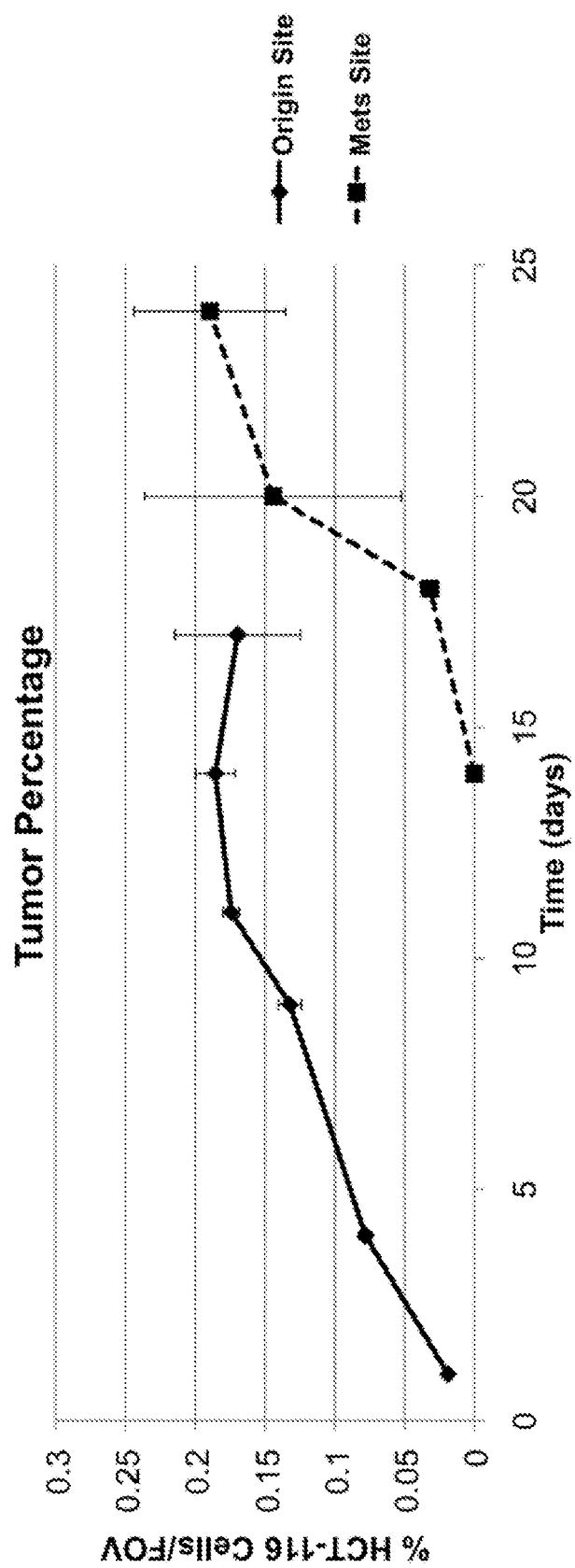

Organoids were fabricated by cell encapsulation (FIG. 1A) using a hyaluronic acid (HA) and gelatin-based hydrogel, HyStem that has been employed extensively in tissue engineering and regenerative medicine[16, 24] in applications such as 3-D culture,[11, 15] tumor models,[10] and biofabrication techniques.[12-14] Modulation of the crosslinker geometry (linear, 4-arm, and 8-arm) can be used for controlling organoid elastic modulus, which will be described at a later point. Each microfluidic device consisted of two circular chambers (10 mm diameter, 3 mm thick), connected by a fluidic channel, fabricated using conventional soft lithography, replica molding, and layer-by-layer stacking (FIG. 1B).[23] Each set of chambers had inlets and outlets connected to a micro-peristaltic pump and media reservoir for driving flow through the circuit (FIG. 1C-D). In the sealed devices, 25 µL gut-tumor organoids and liver organoids were formed and then maintained under constant 10 µL/min flow, supplied from the reservoir by the micro-peristaltic pump. Over time in culture RFP-labeled HCT-116 cells comprising the tumor foci within the primary organoids proliferated and the RFP-positive tumor regions grew in size until dissemination from the organoid into circulation, typically around day 14 of culture (FIG. 2A). After entering circulation, metastatic cells were able to reach the secondary liver organoid constructs, engraft, and invade them via multicellular protrusions and aggregates (FIG. 2B) that continued to proliferate. Time from dissemination to engraftment was variable, but typically occurred within 2-3 days following dissemination into the circulation. Percentage of organoid area occupied by tumor was determined assessing composite images at each site (FIG. 2C) using custom MatLab segmentation code, further demonstrating the trend of tumor growth in the primary organoid. Fluorescent HCT-116 cells occupied a low percentage of the field of views assessed at day 1 (less than 0.05%), but proliferated over time, resulting in nearly 20% of field of views assessed. Importantly, this data also shows the initiation and continuation of tumor growth at the metastatic downstream site following colonization. In this second growth curve, zero HCT-116 cells were observed on day 14, which is when we first observed tumor cells entering circulation, but they quickly establish a foothold by day 18 and rapidly increase in number and tumor percentage over the following 6 days.

Metastasized Colon Carcinoma Tumor Foci Display Markers of Tumorigenic and Mesenchymal Phenotype.

Figures 3A, 3B, 3C:
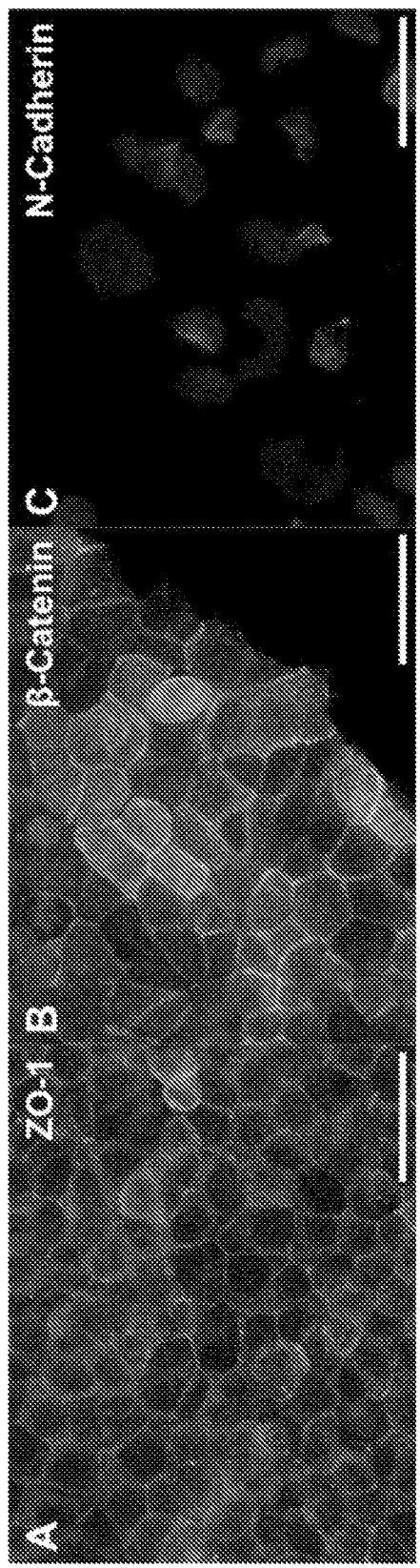
FIG. 3. Expression of cell surface markers and MMP in HCT-116 cells on 2-D tissue culture plastic. HCT-116 cells on tissue culture plastic presented membrane-bound A) ZO-1 and B) β-catenin. Conversely, in 2-D HCT-116 cells fail to express C) N-cadherin, thus suggesting an epithelial phenotype in 2-D, rather than a mesenchymal and metastatic phenotype, demonstrating the lack of physiological accuracy in 2-D cancer cell cultures. Scale bars—100 µM.

After observing engraftment and invasion into the liver organoids, the secondary site constructs containing metastases were fixed and processed to generate tissue sections for immunostaining protocols. The HepG2-based liver regions of the constructs (identified by lack of RFP) showed typical epithelial phenotype. These regions showed cells with ZO-1 tight junction proteins, β-catenin and vinculin, all markers of cell-cell adhesion, with focused expression around the cell membranes. In metastatic regions, highlighted by RFP, ZO-1, 13-catenin, and vinculin were generally not expressed along the cell membrane (data not shown). This lack of cell-cell binding suggests that the HCT-116 cells had a motile phenotype, which was expected as they had migrated to form these metastases.[25, 26] Interestingly, there was positive β-catenin staining in the cytoplasmic and nuclear regions of the HCT-116 cells—a phenomenon commonly described in epithelial to mesenchymal transition (EMT) when the WNT/β-catenin pathway is activated. Activation results in β-catenin traveling to the nucleus and acting as a transcription factor that can induce invasive metastatic phenotypes.[27-29] Additionally, N-cadherin and PCNA stained positive in tumor regions indicating a mesenchymal and proliferative phenotype (data not shown).[30] In comparison, HCT-116 cells cultured on 2-D tissue culture plastic appeared epithelial, showing positive expression of membrane-bound ZO-1 and β-catenin, failing to express N-cadherin (FIG. 3), thus supporting the necessity to employ 3-D systems to recapitulate tumor biology with sufficient accuracy.

These data indicate that our MOC system provides a facsimile of the logistics that occur during metastasis from the gut to the liver. Furthermore, when we assess the metastases in the liver organoids we see evidence of a clear distinction between metastatic RFP-positive regions and RFP-negative liver regions, which correspond with metastatic/mesenchymal and epithelial marker profiles, respectively.

Tumor Cell Migration in 3-D Responds to Changes in Environmental Mechanical Properties and Drug Treatments.

This system, comprised of a tunable hydrogel system, a closed circulatory system with a reservoir for easily introducing new media or other substances, and a clear housing for imaging, is therefore a powerful tool with which one can manipulate the system and assess downstream results, investigate biological mechanisms at play, and perform drug testing studies. To demonstrate the utility of this system we have begun performing such experiments. In one application, we have used this platform to explore the influence of physical microenvironment parameters on metastatic invasion. In another application, we have begun employing the MOC system to determine whether established anti-cancer drugs have the same effects in our system as they do in human patients. If this correlation can be validated, we believe the MOC system can then be robustly implemented in drug candidate screening, and later adapted to personal medicine as a predictive tool by incorporating patient-derived tumor biopsies.

Figure 4A:
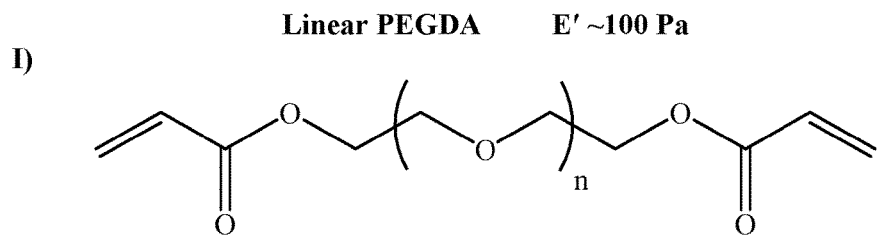
FIG. 4. The effect of tissue and tumor microenvironment elastic modulus on metastatic migration of HCT116 cells in 3-D. A) Using acrylate-functionalized PEG-based crosslinkers of varying geometry allows for manipulation of hydrogel-based organoid and tumor mechanical properties. Rheological data demonstrates statistically different (* $p<0.05$) shear elastic moduli of hydrogels created using these crosslinkers. B) HCT116 cells were embedded in a central stiff gel core of 4.5 kPa surrounded by soft 100 Pa hydrogel-based tissue construct (left), or in a soft 100 Pa core surrounded by a stiff 4.5 kPa hydrogel-based tissue construct (right). C) Top-down, D) side, and (E) isometric macro-confocal images of tumors and space above the tumors. Stiff-core, soft environment tumors grow, but remain primarily at the tumor's location. Soft-core, stiff environment tumors exhibit increased migration outwards from the tumor into the stiff environment in the form of large multicellular protrusions and aggregates.
Figure 4A:
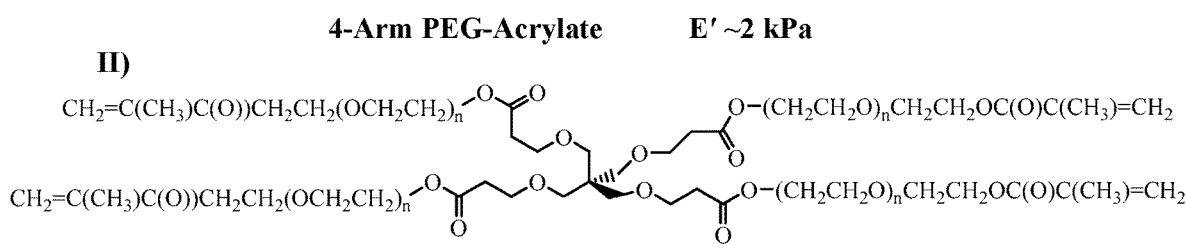
Figure 4A:
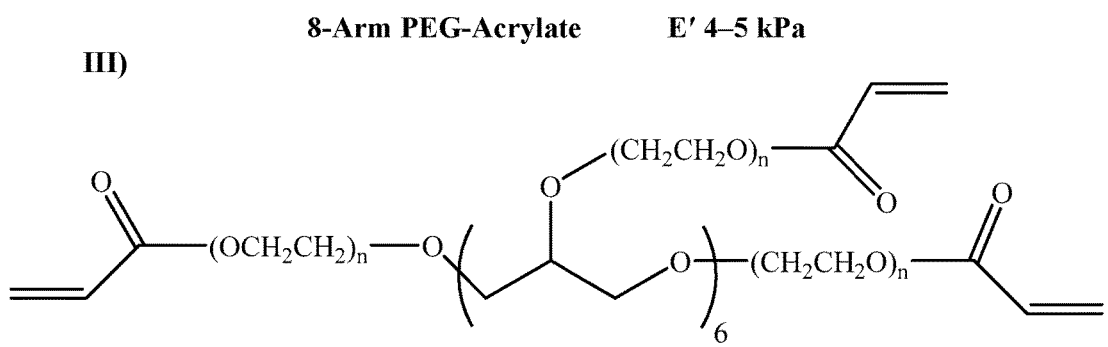
Figure 4A:
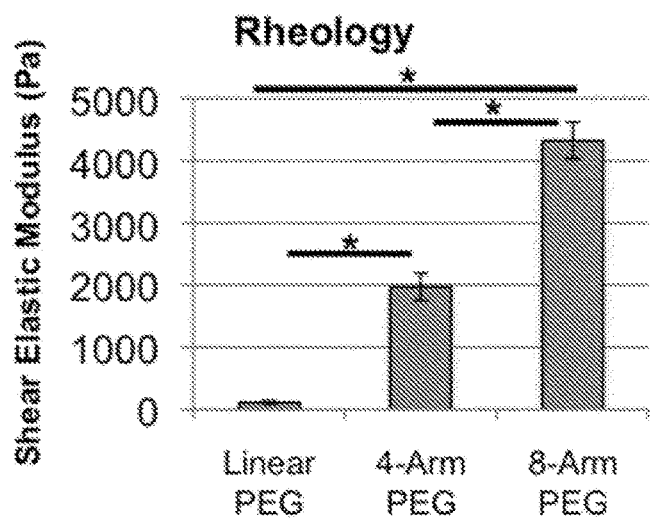
Figures 4B, 4C, 4D, 4E:
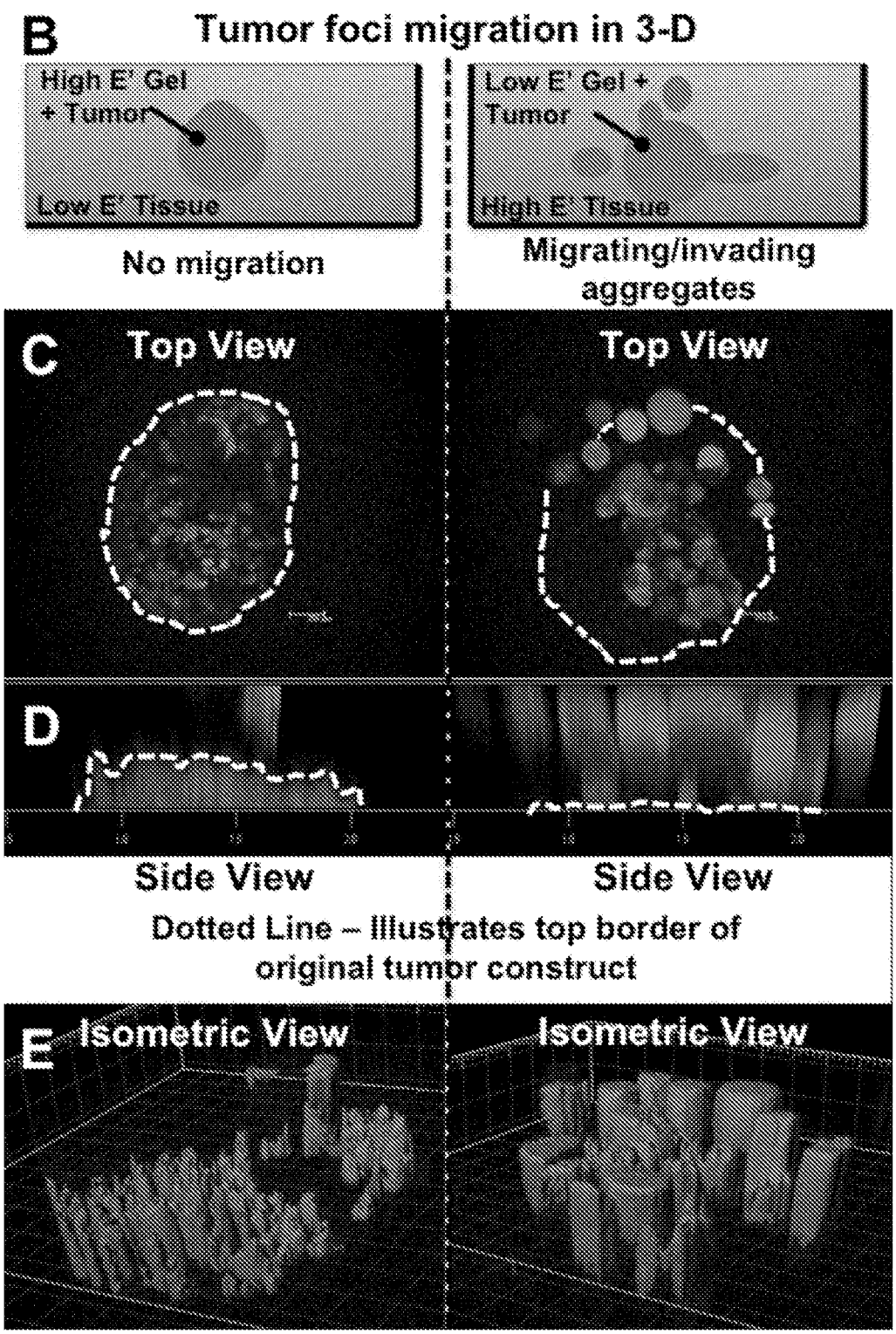

The modular nature of the hydrogel system employed is beneficial as it supports the ability to swap crosslinking agents, thereby allowing control over tissue and tumor elastic modulus E' or the shear elastic modulus G' by altering the crosslinker geometry, which changes the effective crosslinking density within the hydrogel network, subsequently changing the elastic modulus.[14] By using the linear PEGDA crosslinker described above (MW 3.4 kDa), hydrogels form with G' of approximately 100 Pa. However, by using an 8-arm PEG acrylate crosslinker instead, G' values of approximately 4500 Pa can be achieved (FIG. 4A). Use of a 4-arm crosslinker results in a hydrogel with G' near 2000 Pa. By employing these 3-D environments in our metastasis platform, we observed that manipulation of these mechanical properties had a profound effect on HCT-116 migratory behavior. HCT-116 tumor foci were created with discrete microenvironment stiffness levels (100 Pa or 4500 Pa) inside of surrounding hydrogel of discrete stiffness (100 Pa or 4500 Pa) (FIG. 4B). FIG. 4C-E show macro-confocal top-down views, side views, and isometric views of stiff tumor constructs in soft hydrogel (condition 1) or soft tumor constructs in stiff hydrogel (condition 2). In condition 1, we observed some growth of cells near the top interface of the tumors into the surrounding hydrogel. However, in condition 2, we observed migration of large multicellular protrusions and aggregates up and outward from the top of the tumor constructs. This suggests to us that the tissue or tumor stiffness levels can induce or prime tumor cells for increased migratory and invasive behavior, perhaps accelerating metastasis. Interestingly, it was demonstrated in a mouse model that normal tissue supported invasive metastases, linked to upregulation of the WNT pathway. Conversely, decreased E' of tissue in a knockout mouse model, in which collagen crosslinking was decreased, the same metastatic tumors failed to metastasize, but grew in their original locations.[31] This concept of physical parameter influence on tumor invasiveness may give way to new targets of intervention. Perhaps one can artificially induce altered tissue mechanical properties temporarily, thus reducing the likelihood of metastasis. Alternatively, the physical parameters of tumors and their surrounding environments may at the very least serve as biomarkers that are indicative of tumor malignancy and the probability of metastasis.

Figure 5A:
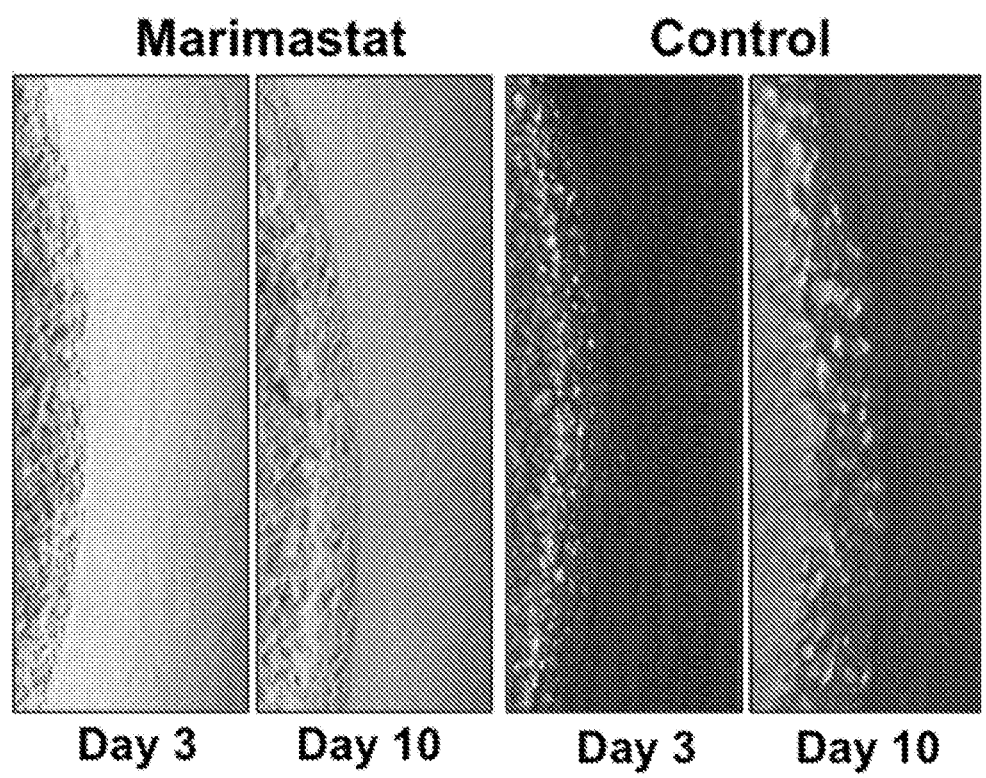
FIG. 5. The effects of Marimastat on HCT-116 migration. A) Marimastat prevents outward growth of aggregates from HCT-116 tumor constructs in 3-D, while control conditions do not. B) Migration of HCT-116 cells quantified by length in pixel counts. Significance: * $p<0.05$ between experimental groups at each time point.
Figure 5B:
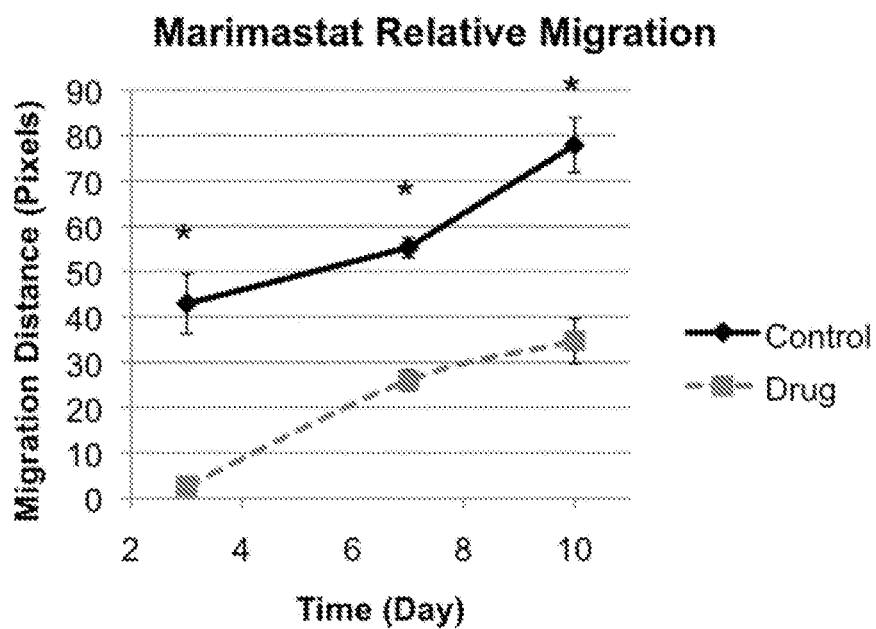
Figure 6A:
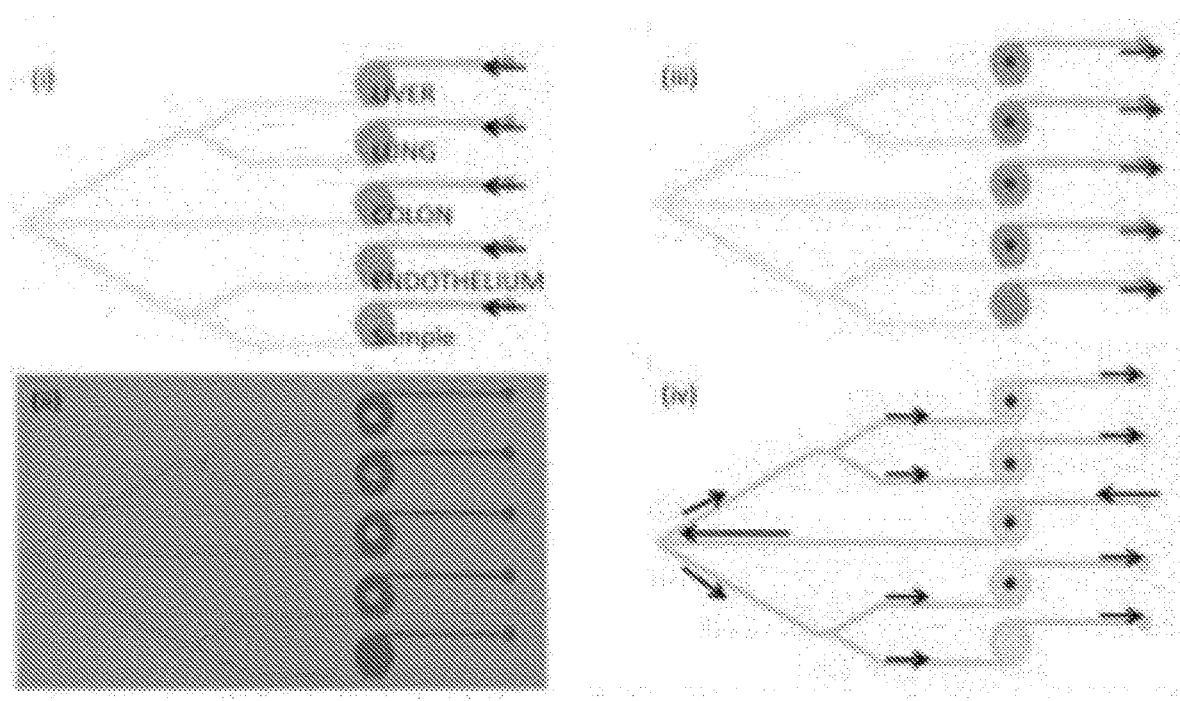
FIG. 6. (A) Schematic workflow of the fabrication of each organ construct by in situ patterning. (i) Each chamber is filled with their correspondent cells/HA mixture (pink) through their correspondent channel (ii) In situ patterned is achieved by UV crosslink through photomask (grey). (iii-iv). The un-crosslink solution is removed. The media flow of the system start at the colon construct and stream into the liver, lung, endothelium, and sample. (B) Viability was assessed by Live & dead assay, where live cells were stained in green and dead red. Concentrations of urea (C) and albumin (D) in the control (time zero), colon-sample and liver media (both on day 7) were measured in each organ's collecting reservoir.
Figure 6B:
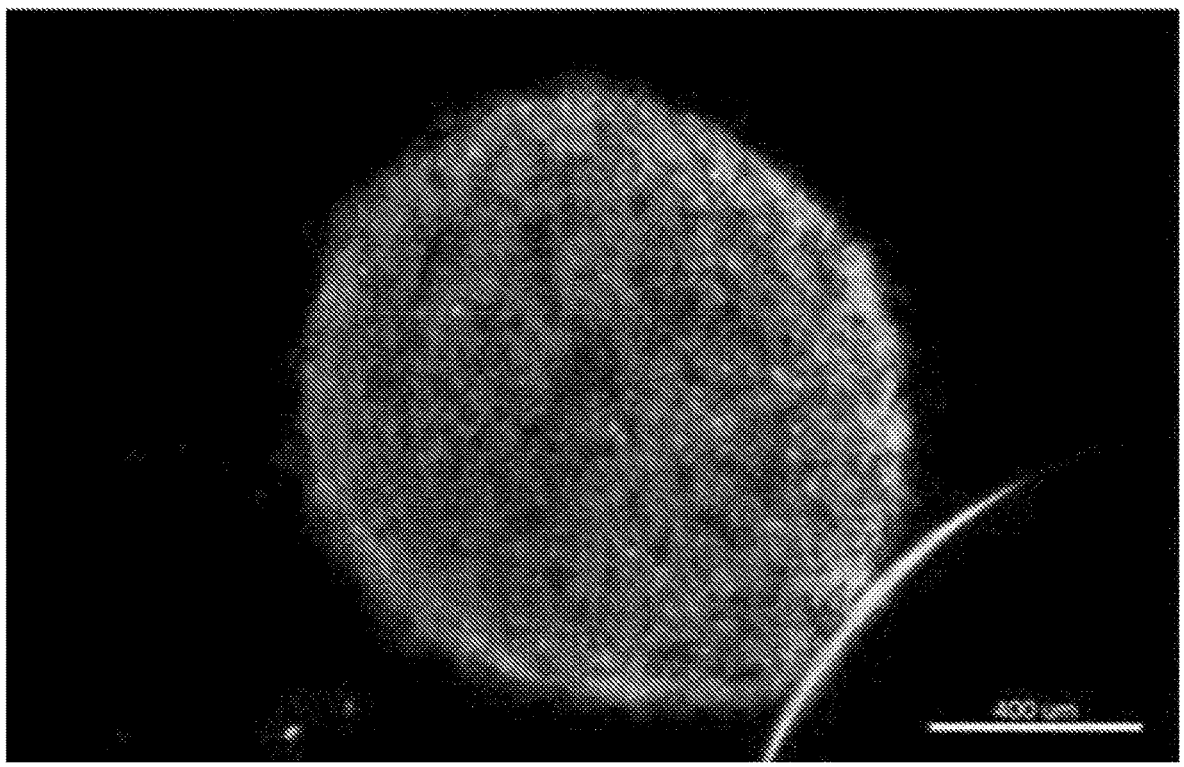
Figure 6C:
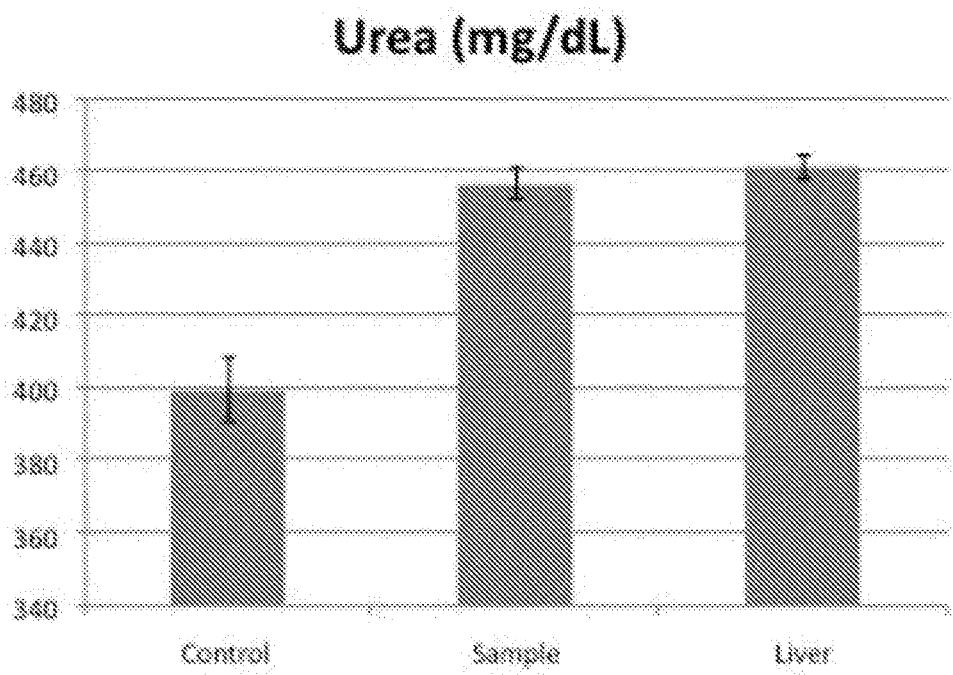
Figure 6D:
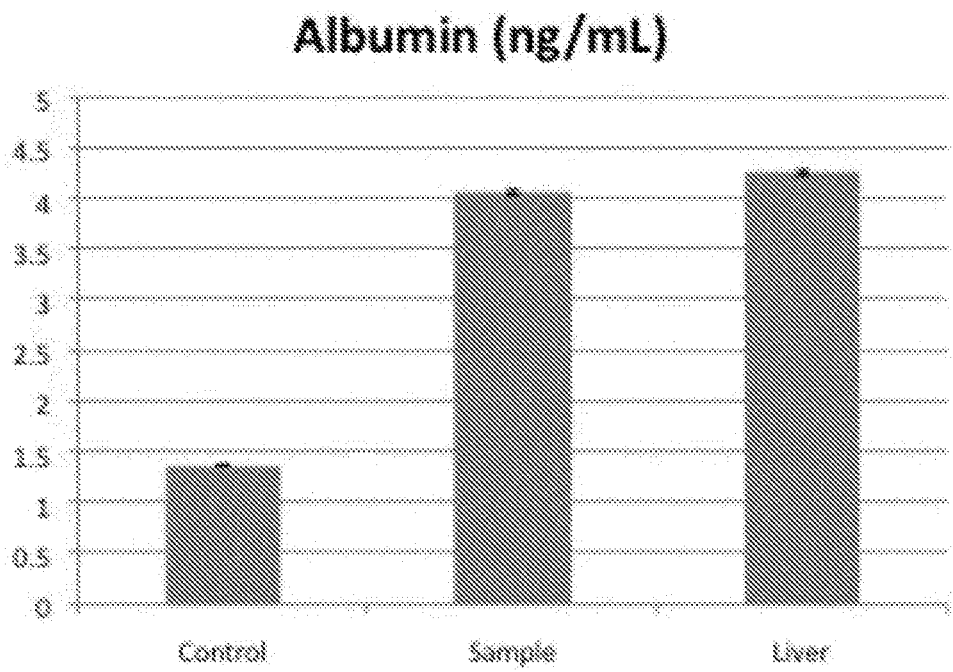

To demonstrate the use of this system for drug testing, we showed that in the HCT-116 constructs Marimastat can in fact reduce tumor cell invasion into the surrounding environment (FIG. 5). Furthermore, this test also acted as validation of our metastasis observations described in FIG. 2, demonstrating that the tumors in the MOC respond as expected to a matrix metalloproteinase inhibiting drug. Tumor organoids were created as described, using the second condition described above (soft tumor [~100 Pa], stiff tissue [~4500 Pa]), which exacerbated metastatic invasion into the surrounding 3-D environment. One half of the prepared systems received normal DMEM, while the other half received 50 μM Marimastat (Sigma) in DMEM. Overlaid fluorescent and brightfield images were captured on day 3, day 7, and day 10, from which distances of migration of cells out of the tumor were determined over time. FIG. 5A shows overlays from day 10, illustrating the increased presence of RFP-positive multicellular HCT-116 aggregates moving away from the tumor core in the no drug condition in comparison to the Marimastat group in which fewer RFP-positive cell aggregates are present. FIG. 5B depicts the quantification of this migratory activity, in which the no drug control condition shows significantly increased migration distance of number pixels at each time point. In other words, administration of Marimastat significantly prevented migration of metastatic HCT-116 cells, most likely through inhibition of MMPs.[21, 32] Additionally, although not performed in this specific system, we have recently shown that similar 3-D tumor organoid systems respond to 5-FU in similar ways that in vivo tissues do.[33]

Discussion

The concept of a MOC system using 3-D organoids addresses many current shortcomings in cancer research. First and foremost, animal models are not optimal for quick studies and high-throughput scenarios because of the often long experimental time courses and the difficulty of scaling study sizes. They only support the capability for limited mechanistic manipulation and do not always offer simple ways to monitor the results. Perhaps, most importantly, results in animals are not necessarily predictive of results in humans. The other most common tool in cancer research, traditional 2-D cultures, fails to recapitulate the 3-D microenvironment of in vivo tissues.[3] For a number of reasons, the drug doses that are found to be effective in 2-D are often less effective when scaled to patients.[4, 5] The MOC system addresses these problems by using human-derived cells and employing them in a 3-D hydrogel-supported environment. We observed appropriate cell-cell interactions depending on host tissue or tumor regions, and the tumors respond appropriately to drugs. Another lacking aspect in many research approaches is failure to consider both the primary tumors site and the downstream site, or sites, of metastasis. The MOC was conceptualized to specifically include tissue-engineered 3-D organoids representing these sites, allowing researchers to recapitulate the kinetics of metastatic migration from an originating tissue to a target tissue. This is important because the phenotype of cells in the originating tumors and the metastases can vary significantly.[21, 22]

Having the ability to study both tumor types and microenvironments is integral to accurately model metastasis in its entirety. Our system successfully supports tumor growth in primary site organoids over time. The metastatic colon carcinoma cells we employed, HCT-116, were capable of breaking out of the organoid and then entering circulation. Furthermore, and importantly, the circulating cells engrafted into the downstream organoid within the device, invading the organoid's 3-D space, and continuing to grow in size. This is consistent with a liver-tumor spheroid-based organoid model we developed recently, in which the metastatic tumor grew over time within the liver host tissue.[6] Importantly, immunostaining data from this and the previously referenced study both demonstrate a clear distinction between the epithelial organoid environment and mesenchymal marker-expressing tumor foci. Notably, this is dramatically different from when HCT-116 cells are cultured on traditional 2-D tissue culture plastic, where they appear epithelial instead of mesenchymal and metastatic in nature. The data we have described here is a collection of the first validation and verification experiments performed with the system. However, we also demonstrated the ability to manipulate the system using modular hydrogel technology to create tumor microenvironment changes or by administering a chemotherapy drug, after which the effects of these factors were able to be observed and documented in a straightforward fashion, thus demonstrating the significant potential that we believe this platform possesses to be used in a multitude of mechanistic and screening applications

REFERENCES

1. I. J. Fidler, S. J. Kim and R. R. Langley, *J Cell Biochem,* 2007, 101, 927-936.
2. R. R. Langley and I. J. Fidler, *Endocr Rev,* 2007, 28, 297-321.
3. L. A. Kunz-Schughart, J. P. Freyer, F. Hofstaedter and R. Ebner, *J Biomol Screen,* 2004, 9, 273-285.
4. W. J. Ho, E. A. Pham, J. W. Kim, C. W. Ng, J. H. Kim, D. T. Kamei and B. M. Wu, *Cancer science,* 2010, 101, 2637-2643.
5. M. Drewitz, M. Helbling, N. Fried, M. Bieri, W. Moritz, J. Lichtenberg and J. M. Kelm, *Biotechnol J,* 2011, 6, 1488-1496.
6. A. Skardal, M. Devarasetty, C. Rodman, A. Atala and S. Soker, *Ann Biomed Eng,* 2015.
7. A. Polini, L. Prodanov, N. S. Bhise, V. Manoharan, M. R. Dokmeci and A. Khademhosseini, *Expert opinion on drug discovery,* 2014, 9, 335-352.
8. K. H. Benam, S. Dauth, B. Hassell, A. Herland, A. Jain, K. J. Jang, K. Karalis, H. J. Kim, L. MacQueen, R. Mahmoodian, S. Musah, Y. S. Torisawa, A. D. van der Meer, R. Villenave, M. Yadid, K. K. Parker and D. E. Ingber, *Annual review of pathology,* 2015, 10, 195-262.
9. S. V. Murphy, A. Skardal and A. Atala, *J Biomed Mater Res A,* 2013, 101, 272-284.
10. A. Skardal, S. F. Sarker, A. Crabbe, C. A. Nickerson and G. D. Prestwich, *Biomaterials,* 2010, 31, 8426-8435.
11. A. Skardal, L. Smith, S. Bharadwaj, A. Atala, S. Soker and Y. Zhang, *Biomaterials,* 2012, 33, 4565-4575.
12. A. Skardal, J. Zhang, L. McCoard, S. Oottamasathien and G. D. Prestwich, *Adv Mater,* 2010, 22, 4736-4740.
13. A. Skardal, J. Zhang, L. McCoard, X. Xu, S. Oottamasathien and G. D. Prestwich, *Tissue Eng Part A,* 2010, 16, 2675-2685.
14. A. Skardal, J. Zhang and G. D. Prestwich, *Biomaterials,* 2010, 31, 6173-6181.
15. J. Zhang, A. Skardal and G. D. Prestwich, *Biomaterials,* 2008, 29, 4521-4531.
16. J. A. Burdick and G. D. Prestwich, *Adv Mater,* 2011, 23, H41-56.
17. G. D. Prestwich, *J Cell Biochem,* 2007, 101, 1370-1383.
18. G. D. Prestwich, *Acc. Chem. Res.,* 2008, 41, 139-148.
19. G. D. Prestwich and J. W. Kuo, *Curr Pharm Biotechnol,* 2008, 9, 242-245.
20. D. D. Allison and K. J. Grande-Allen, *Tissue Eng,* 2006, 12, 2131-2140.
21. G. Karakiulakis, C. Papanikolaou, S. M. Jankovic, A. Aletras, E. Papakonstantinou, E. Vretou and V. Mirtsou-Fidani, *Invasion & metastasis,* 1997, 17, 158-168.
22. C. Franci, J. Zhou, Z. Jiang, Z. Modrusan, Z. Good, E. Jackson and H. Kouros-Mehr, *PLoS One,* 2013, 8, e58183.
23. Y. Xia and G. M. Whitesides, *Annu Rev Mater Scie,* 1998, 28, 153-184.
24. G. D. Prestwich, *J Control Release,* 2011, 155, 193-199.
25. N. Gavert and A. Ben-Ze'ev, *F1000 biology reports,* 2010, 2, 86.
26. D. J. McGrail, R. Mezencev, Q. M. Kieu, J. F. McDonald and M. R. Dawson, *FASEB J,* 2014.
27. J. Behrens, *Ann N Y Acad Sci,* 2000, 910, 21-33; discussion 33-25.
28. H. Brantjes, N. Barker, J. van Es and H. Clevers, *Biol Chem,* 2002, 383, 255-261.
29. S. Orsulic, O. Huber, H. Aberle, S. Arnold and R. Kemler, *J Cell Sci,* 1999, 112 (Pt 8), 1237-1245.
30. M. Tania, M. A. Khan and J. Fu, *Tumour biology: the journal of the International Society for Oncodevelopmental Biology and Medicine,* 2014, 35, 7335-7342.
31. K. R. Levental, H. Yu, L. Kass, J. N. Lakins, M. Egeblad, J. T. Erler, S. F. Fong, K. Csiszar, A. Giaccia, W. Weninger, M. Yamauchi, D. L. Gasser and V. M. Weaver, *Cell,* 2009, 139, 891-906.
32. M. H. Zaman, L. M. Trapani, A. L. Sieminski, D. Mackellar, H. Gong, R. D. Kamm, A. Wells, D. A. Lauffenburger and P. Matsudaira, *Proc Natl Acad Sci USA,* 2006, 103, 10889-10894.
33. A. Skardal, M. Devarasetty, C. Rodman, A. Atala and S. Soker, *Ann Biomed Eng,* 2015, In Press.
34. R. Lang, M. M. Stern, L. Smith, Y. Liu, S. Bharadwaj, G. Liu, P. M. Baptista, C. R. Bergman, S. Soker, J. J. Yoo, A. Atala and Y. Zhang, *Biomaterials,* 2011, 32, 7042-7052.

Example 2

Multiple Organ-On-a-Chip Platform for Metastasis Dynamic Studies

Cellular phenomena involved in cancer metastasis have been studied under the "seed and soil" hypothesis or defined by anatomical and mechanical routing [1]. In the case of colorectal cancer (CRC), tumor cells predominantly metastasize to the liver, likely due to proximity lymphatic drainage. Advances in modular and microfluidic layouts of organ-on-achip (OC) platforms, alongside integrated extracellular matrix (ECM) based scaffolds, help to recapitulate in vivo environmental composition and mechanics [2-3]. In situ patterned hyaluronic acid hydrogel organs; HepG2/C3A (liver), A549 (lung), HUVEC (endothelium) and HCT 116 (colon) cells, were set up in equidistant microfluidic perfuse chambers. We achieved the fabrication of a highly precise multiple OC device with >500 µm in situ patterned organs embedded in a 3D ECM based scaffold.

As shown in FIG. 6, we fabricated a multiple organs platform with 3D ECM constructs and connected through an equidistant microfluidic system. The organ constructs were secluded in individual microfluidic chambers using in situ patterning and can maintain viability, so far, for a week. The state of health of each construct was assessed by representative metabolites. The system provides in vitro mimicry of in vivo environmental composition and physical flow. The platform is useful for assessing the effects of the fluidic network-design versus tissue environmental factors on colorectal cancer metastasis.

REFERENCES

1. Skardal, A. *Biomaterial.* 33: 4565-4575 (2012).
2. Skardal, A. *Biotechnol Bioeng.* 9999: 1-13 (2016).
3. Oleaga, C. *Scientific Reports.* 6:20030 (2016).

Example 3

Figure 7:
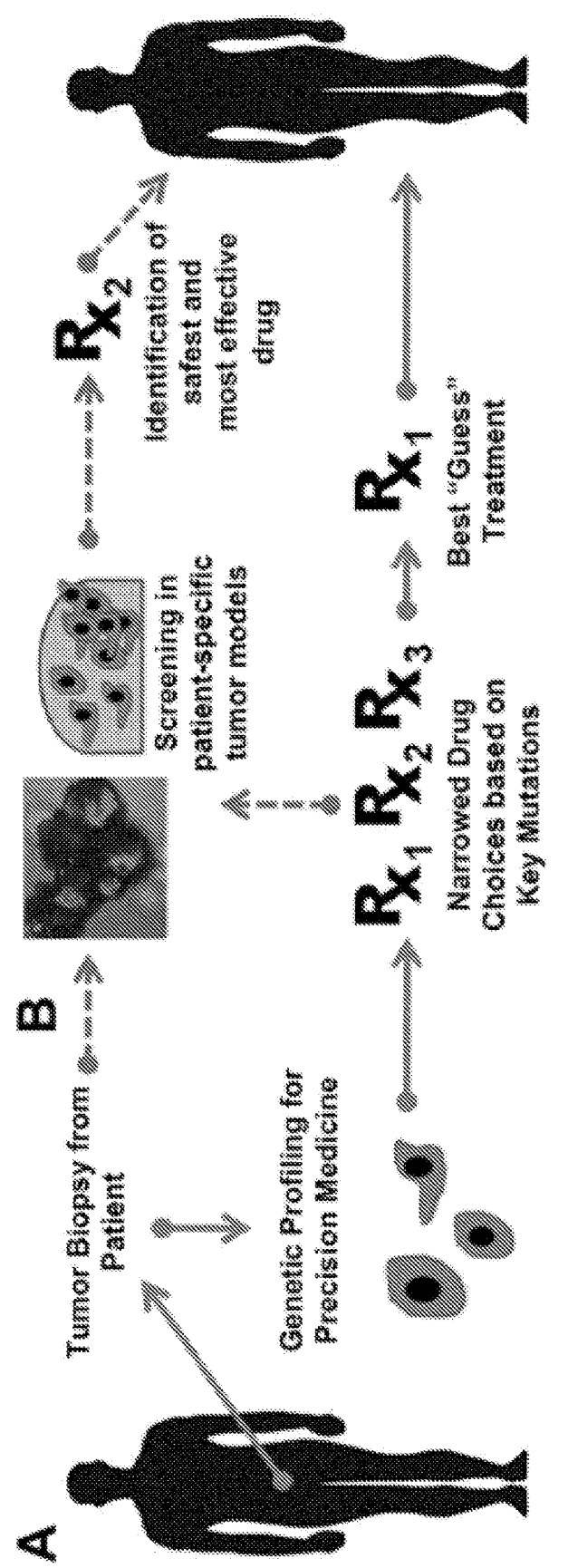
FIG. 7. Schematic illustration of a tumor organoid and metastasis platform implemented for personalized medicine oncology.

A Tumor Organoid-On-a-Chip Platform for Screening Precision Medicine-Driven Therapies Precision medicine—identifying treatments for patients based on their tumor genetic profiles—has gained significant traction. However, in practice, even after identification of key mutations, oncologists are often left with several drug options, suggesting that systems are necessary for prediction of effective treatments. As schematically illustrated in FIG. 7, methods and apparatus as described herein above provide a platform for translating tumor organoids towards use in precision medicine by demonstrating nuanced mutation-specific drug responses using a "toolbox" of tumor cell lines with mutations commonly observed in the clinic. In a non-limiting example, colorectal cancer (CRC) organoids were created by encapsulating CRC cells (Caco2 and SW480—WT; HCT116—KRASMT; and HT29—BRAFMT) in hyaluronic acid and gelatin hydrogels in microfluidic devices. Each type of CRC organoid was then subjected to a panel of clinical CRC drugs: 5-FU or oxaliplatin (1st line drugs effective in WT tumors), Tramatinib (an EGFR pathway drug effective in KRASMT tumors), and sorafenib or regorafenib (EGFR pathway drugs effective in BRAFMT tumors). Following 48-hour treatments, organoids were assessed for mitochondrial metabolism by MTS assays. There appeared to be clear differences in drug responsiveness that correlated with EGFR genetic states. Both Caco2 and SW480 organoids (WT) were particularly sensitive to 5-FU, and less so to the other drugs. HCT116 organoids were particularly sensitive both to 5-FU and to sorafenib. HT29 organoids were in general more resistant across the board, but displayed a trend of slight sensitivity to regorafenib. The results described here demonstrate that 3D tumor organoids can be successfully employed for screening drugs based on tumor genetic profiles. The methods and systems are useful for assessing metastasis kinetics, as well as transitioning to patient biopsy-derived tumor cells, and can be implemented to screen potentially effective drugs using tumor-on-a-chip systems such as described above customized to individual patients, determining the treatments that are the most effective and safest to administer.

REFERENCES

1. Skardal A, et al., *Biofabrication*. 7(3): 031001 (2015).
2. Skardal A, et al., *Biotechnol Bioeng*. (2016).
3. Skardal A, et al., *Ann Biomed Eng*. 43(10): 2361-73 (2015).

The foregoing is illustrative of the present invention, and is not to be construed as limiting thereof. The invention is defined by the following claims, with equivalents of the claims to be included therein.

That which is claimed is:

1. An apparatus comprising: a primary chamber including a first organoid that comprises mammalian cancer cells and a first hydrogel, wherein the first organoid is present within the first hydrogel;
   at least one secondary chamber, wherein the at least one secondary chamber comprises a second organoid and a second hydrogel, wherein the second organoid is present within the second hydrogel;
   at least one primary conduit connecting said primary and secondary chambers and providing fluid communication therebetween;
   a fluid circuit that, in operation, is a closed fluidic system and provides fluid flow through the primary chamber and first organoid, then through the at least one primary conduit, next through at least one branching conduit that branches off of the at least one primary conduit, and then to the at least one secondary chamber and second organoid in the same fluid path, wherein the circuit comprises the at least one primary conduit connecting said primary and secondary chambers and providing fluid communication therebetween; and
   a growth media in said primary chamber, each of said secondary chamber(s), and each of said primary conduit(s), wherein said first and second hydrogels comprise thiolated hyaluronic acid, thiolated gelatin, and polyethylene glycol diacrylate.

2. The apparatus of claim 1, wherein said first organoid further comprises:
   mammalian tissue cells, optionally in an extracellular matrix; or
   an extracellular matrix carrying said cancer cells;
   optionally, a layer of blood vessel or lymphatic endothelial cells at least partially around or above said first organoid; and
   optionally, immune system cells.

3. The apparatus of claim 1, further comprising an optically transparent window in said primary and/or secondary chambers.

4. The apparatus of claim 1, wherein said first organoid comprises a layer of blood vessel or lymphatic endothelial cells at least partially around or above said first organoid.

5. The apparatus of claim 1, further comprising a fluid inlet connected to said primary chamber and a fluid outlet connected to each of said secondary chamber(s).

6. The apparatus of claim 1, wherein said secondary chambers are connected to one another in series, in parallel, or in combinations thereof.

7. The apparatus of claim 1, wherein said cancer cells express a detectable compound.

8. The apparatus of claim 1, wherein the second organoid comprises a lung, lymph node, liver, bone, central nerve, skin, smooth muscle, or skeletal muscle organoid.

9. The apparatus of claim 1, wherein:
   said first organoid comprises intestinal epithelial cells in combination with colon carcinoma cells, and said second organoid comprises a liver, central nerve, peripheral nerve, or bone organoid;
   said first organoid comprises lung airway epithelial cells in combination with either small cell lung cancer or lung adenocarcinoma cells, and said second organoid comprises a peripheral nerve, central nerve, liver, or bone organoid;
   said first organoid comprises mammary gland epithelial cells in combination with breast carcinoma, adenocarcinoma or sarcoma cells, and said second organoid comprises a liver, peripheral nerve, central nerve, bone, lung, lymph node, smooth muscle, skeletal muscle, or skin organoid;
   said first organoid comprises prostate gland cells in combination with prostate acinar or ductal adenocarcinoma cells, and said second organoid comprises a liver, peripheral nerve, central nerve, bone, lung, or lymph node organoid; or
   said first organoid comprises keratinocytes, optionally melanocytes, and melanoma cells in combination, and said second organoid comprises a liver, peripheral nerve, central nerve, bone, lung, skin or lymph node organoid;

said first organoid comprises central nervous system tumor cells optionally differentiated central nervous system cells and said second organoid comprises a central nerve organoid;

said first organoid comprises liver cells in combination with hepatoma or hepatocellular carcinoma cells, and said second organoid comprises a peripheral nerve, central nerve, lymph node, lung, or bone organoid;

said first organoid comprises pancreatic cells in combination with pancreatic adenocarcinoma cells, and said second organoid comprises a peripheral nerve, central nerve, lymph node, liver, lung, or bone organoid;

the first organoid comprises endometrial cells, and optionally myometrial cells, in combination with endometrial carcinoma, uterine sarcoma, or uterine carcinosarcoma cells, and the second organoid comprises a lung, lymph node, liver, bone, central nerve, skin, smooth muscle, or skeletal muscle organoid; or the first organoid comprises cervical mucosa cells and optionally smooth muscle cells in combination with cervical squamous carcinoma or adenocarcinoma cells, and the second organoid comprises bladder, bone, lung, liver, smooth muscle, skeletal muscle, or intestinal organoid.

10. The apparatus of claim 1, further comprising a pump operatively associated with said primary chamber for circulating said growth media from said primary chamber to said at least one secondary chamber.

11. The apparatus of claim 1, further comprising a growth media reservoir and/or bubble trap operatively associated with said primary chamber.

12. The apparatus of claim 1, further comprising a return conduit operatively associated with said primary and secondary chambers for returning growth media circulated through said at least one secondary chamber to said primary chamber.

13. The apparatus of claim 1, packaged in a container together with a cooling element in said container.

14. The apparatus of claim 1, further comprising a first planar member and a second planar member, wherein the first organoid and the second organoid are each between the first planar member and the second planar member.

15. An apparatus of claim 1 wherein said thiolated hyaluronic add, said thiolated gelatin, and said polyethylene glycol diacrylate are cross-linked.

16. A method of screening a test compound for anti-metastatic activity against cancer cells, comprising the steps of:

providing the apparatus of claim 1;

circulating the growth medium from said primary chamber to said at least one secondary chamber;

administering a test compound to said first organoid; and determining a decrease in the presence of cancer cells in said second organoid, as compared to the number of cancer cells present in said second organoid when said test compound is not administered.

17. The method of claim 16, wherein said cancer cells express a detectable compound, said at least one secondary chamber has an optically transparent window, and said determining step is carried out by detecting said detectable compound through said window.

18. The method of claim 16, wherein said determining step is carried out a plurality of times sequentially spaced from one another.

19. A method of screening a test compound for anti-cancer or anti-metastatic activity against cancer cells in a subject, comprising the steps of:

providing the apparatus of claim 1, wherein said mammalian cancer cells are isolated from said subject;

circulating the growth medium from said primary chamber to said at least one secondary chamber;

administering a test compound to said first organoid; and determining a decrease in the presence of cancer cells in said first organoid and/or said at least one second organoid, as compared to the number of cancer cells present in said first organoid and/or said at least one second organoid when said test compound is not administered.

20. The method of claim 19, wherein said cancer cells express a detectable compound, said primary chamber and at least one secondary chamber have an optically transparent window, and said determining step is carried out by detecting said detectable compound through said window.

21. The method of claim 19, wherein said determining step is carried out a plurality of times sequentially spaced from one another.

* * * * *